United States Patent
Novak et al.

(10) Patent No.: US 12,233,089 B2
(45) Date of Patent: Feb. 25, 2025

(54) FOODS TO PROMOTE BETTER HEALTH AND/OR TO MAINTAIN HOMEOSTASIS AND METHOD OF PRODUCTION THEREOF

(71) Applicant: Vector Vitale IP LLC, North Miami Beach, FL (US)

(72) Inventors: Peter Y. Novak, Sunny Isles Beach, FL (US); Maxim Temnikov, Miami, FL (US)

(73) Assignee: Vector Vitale IP LLC, North Miami Beach, FL (US)

( * ) Notice: Subject to any disclaimer, the term of this patent is extended or adjusted under 35 U.S.C. 154(b) by 0 days.

(21) Appl. No.: 18/436,468

(22) Filed: Feb. 8, 2024

(65) Prior Publication Data

US 2024/0261327 A1    Aug. 8, 2024

Related U.S. Application Data

(60) Continuation of application No. 17/870,026, filed on Jul. 21, 2022, now Pat. No. 11,896,610, which is a division of application No. 17/214,346, filed on Mar. 26, 2021, now Pat. No. 11,433,095.

(51) Int. Cl.

| | |
|---|---|
| *A61K 33/30* | (2006.01) |
| *A01C 21/00* | (2006.01) |
| *A01G 31/00* | (2018.01) |
| *A23K 20/142* | (2016.01) |
| *A23K 20/20* | (2016.01) |
| *A23K 50/30* | (2016.01) |
| *A23K 50/75* | (2016.01) |
| *A23K 50/80* | (2016.01) |
| *A23L 13/40* | (2023.01) |
| *A23L 13/50* | (2016.01) |
| *A23L 15/00* | (2016.01) |
| *A23L 17/00* | (2016.01) |
| *A23L 33/00* | (2016.01) |
| *A23L 33/16* | (2016.01) |
| *A23L 33/175* | (2016.01) |
| *A61K 31/315* | (2006.01) |
| *A61K 33/00* | (2006.01) |
| *A61K 33/06* | (2006.01) |
| *A61K 33/26* | (2006.01) |
| *A61K 35/12* | (2015.01) |
| *A61K 35/57* | (2015.01) |
| *A61K 35/60* | (2006.01) |
| *A61K 36/42* | (2006.01) |
| *A61K 36/73* | (2006.01) |
| *A61K 36/81* | (2006.01) |
| *C05D 9/02* | (2006.01) |
| *C05G 5/23* | (2020.01) |

(52) U.S. Cl.
CPC ............ *A61K 33/30* (2013.01); *A01C 21/007* (2013.01); *A01G 31/00* (2013.01); *A23K 20/142* (2016.05); *A23K 20/30* (2016.05); *A23K 50/30* (2016.05); *A23K 50/75* (2016.05); *A23K 50/80* (2016.05); *A23L 13/428* (2016.08); *A23L 13/432* (2016.08); *A23L 13/55* (2016.08); *A23L 15/30* (2016.08); *A23L 17/00* (2016.08); *A23L 33/16* (2016.08); *A23L 33/175* (2016.08); *A23L 33/40* (2016.08); *A61K 31/315* (2013.01); *A61K 33/00* (2013.01); *A61K 33/06* (2013.01); *A61K 33/26* (2013.01); *A61K 35/12* (2013.01); *A61K 35/57* (2013.01); *A61K 35/60* (2013.01); *A61K 36/42* (2013.01); *A61K 36/73* (2013.01); *A61K 36/81* (2013.01); *C05D 9/02* (2013.01); *C05G 5/23* (2020.02); *A23V 2002/00* (2013.01)

(58) Field of Classification Search
CPC ...................................................... A61K 33/30
See application file for complete search history.

(56) References Cited

U.S. PATENT DOCUMENTS

| | | | |
|---|---|---|---|
| 9,861,659 B2 | 1/2018 | Novak et al. | |
| 10,183,041 B2 | 1/2019 | Novak et al. | |
| 10,226,484 B2 | 3/2019 | Novak et al. | |
| 10,799,530 B1 * | 10/2020 | Novak | A61K 9/0053 |
| 10,933,091 B1 | 3/2021 | Novak et al. | |
| 2003/0211132 A1 | 11/2003 | Ohkawa | |

FOREIGN PATENT DOCUMENTS

| | | |
|---|---|---|
| SU | 1486925 A | 6/1989 |
| WO | 2006085785 A1 | 8/2006 |

OTHER PUBLICATIONS

International Application No. PCT/US2021/024433, Invitation to Pay Additional Fees mailed Jan. 3, 2022, 13 pages.
Chilimba et al., "Assessing Residual Availability of Selenium Applied to Maize Crops in Malawi," Elsevier, vol. 134, Apr. 23, 2012, pp. 11-18.
Arnold et al., Evidence for the Mechanisms of Zinc, Uptake by Rice Using Isotope Fractionation. Plant, Cell and Environment 2010, vol. 33, No. 3, pp. 370-381.
Black, "Magnesium-Isotope Fractionation During Plant Growth," Environmental Science & Technology, 2008, vol. 42, No. 21, pp. 7831-7836.

* cited by examiner

*Primary Examiner* — Qiuwen Mi
(74) *Attorney, Agent, or Firm* — Liang & Hennessey LLP; Stanley D. Liang

(57) ABSTRACT

Engineered food to promote health and maintain homeostasis in a subject and methods of producing the food.

7 Claims, 2 Drawing Sheets

FOODS TO PROMOTE BETTER HEALTH AND/OR TO MAINTAIN HOMEOSTASIS AND METHOD OF PRODUCTION THEREOF

TECHNICAL FIELD

This disclosure relates to engineered food for promoting better health and/or maintaining homeostasis in a subject.

BACKGROUND

Vaccines are virus or bacteria specific and thus are not equipped to protect humans from new infections and even from modified old ones. Mankind has to deal with new and possibly more dangerous infectious agents continuously. Degenerative diseases, such as Parkinson's, Alzheimer's, etc., are major health problems to humans, and are without cure. Maintaining homeostasis and/or promoting health in a subject must be a priority.

SUMMARY

In one aspect, this disclosure provides a method of producing a food product from a plant comprising growing the plant in fertilizer or compost comprising essential chemical elements enriched for lightest stable isotope or isotopes thereof; or foliar feeding the plant a solution comprising essential chemical elements enriched for lightest stable isotope or isotopes thereof; or growing the plant in hydroponics in a solution comprising essential chemical elements enriched for lightest stable isotope or isotopes thereof.

In another aspect, this disclosure provides a method of producing a livestock or a livestock product comprising raising the livestock by feeding the livestock food enriched for lightest stable isotope or isotopes thereof or a solution comprising essential chemical elements enriched for lightest stable isotope or isotopes thereof; or raising the livestock by injecting the livestock intravenously a solution comprising essential chemical elements enriched for lightest stable isotope or isotopes thereof.

In yet another aspect, this disclosure provides a method of producing an aquaculture product or a mariculture product comprising raising the aquaculture product or the mariculture product by feeding the aquaculture product or the mariculture product food or solution comprising essential chemical enriched for lightest stable isotope or isotopes thereof.

In another aspect, this disclosure provides a product of a plant, a livestock, a livestock product, an aquaculture product, or a mariculture product comprising essential chemical elements enriched for lightest stable isotope or isotopes thereof.

In another aspect, this disclosure also provides a product of a plant, a livestock or a livestock product, an aquaculture product or a mariculture product made by a disclosed method.

In another aspect, this disclosure provides a fertilizer or a compost comprising essential chemical elements enriched for lightest stable isotope or isotopes thereof.

This disclosure also provides a method of promoting health or a method of maintaining homeostasis in a subject by feeding the subject one or more food items made from a disclosed product of a plant, food made from a disclosed livestock, food made from a disclosed livestock product, or food made from an aquaculture product or a mariculture product.

Numerous other aspects are provided in accordance with these and other aspects of the invention. Other features and aspects of the present invention will become more fully apparent from the following detailed description and the appended claims.

DETAILED DESCRIPTION

Figure 1:
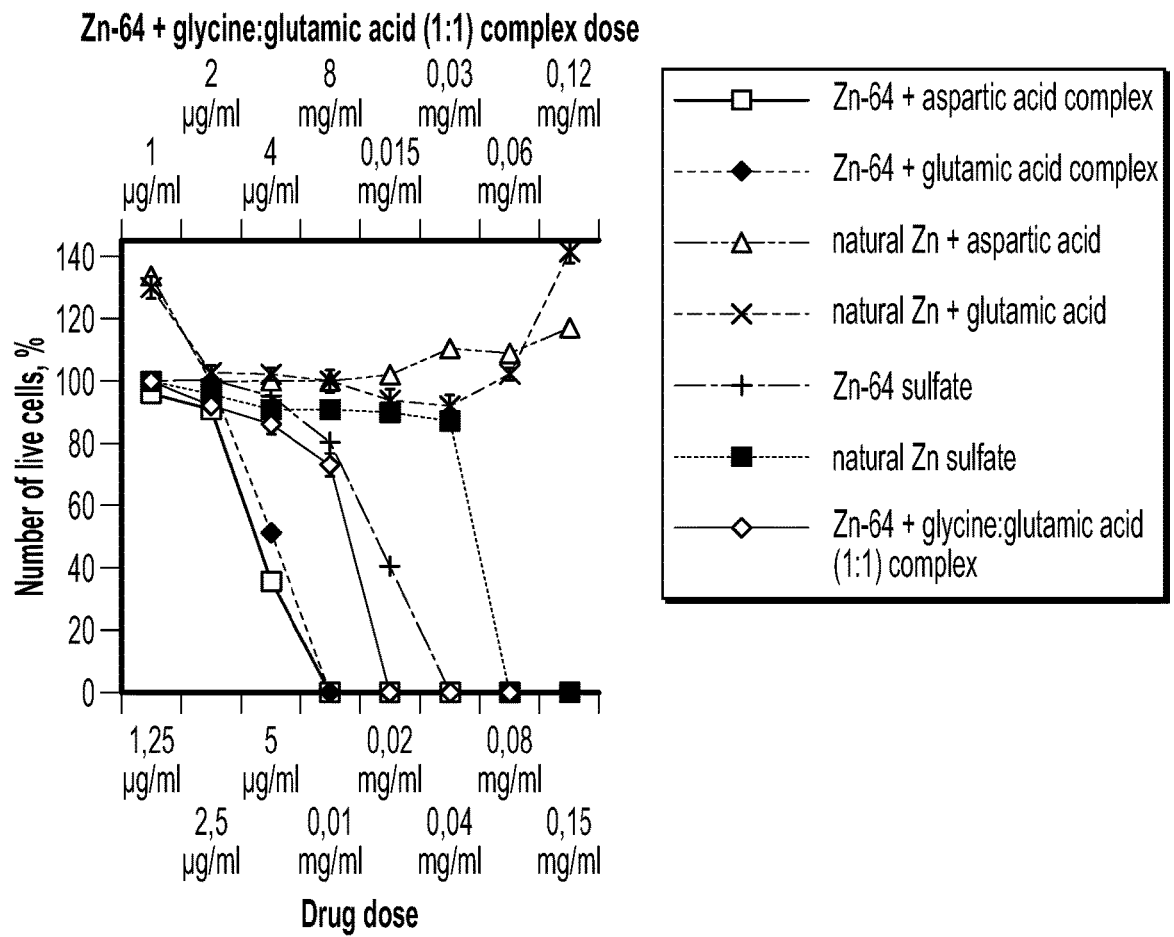
FIG. 1 is a graph showing cytotoxic/cytostatic action of natural zinc and Zn-64 compounds on HL-60 cells.
Figure 2:
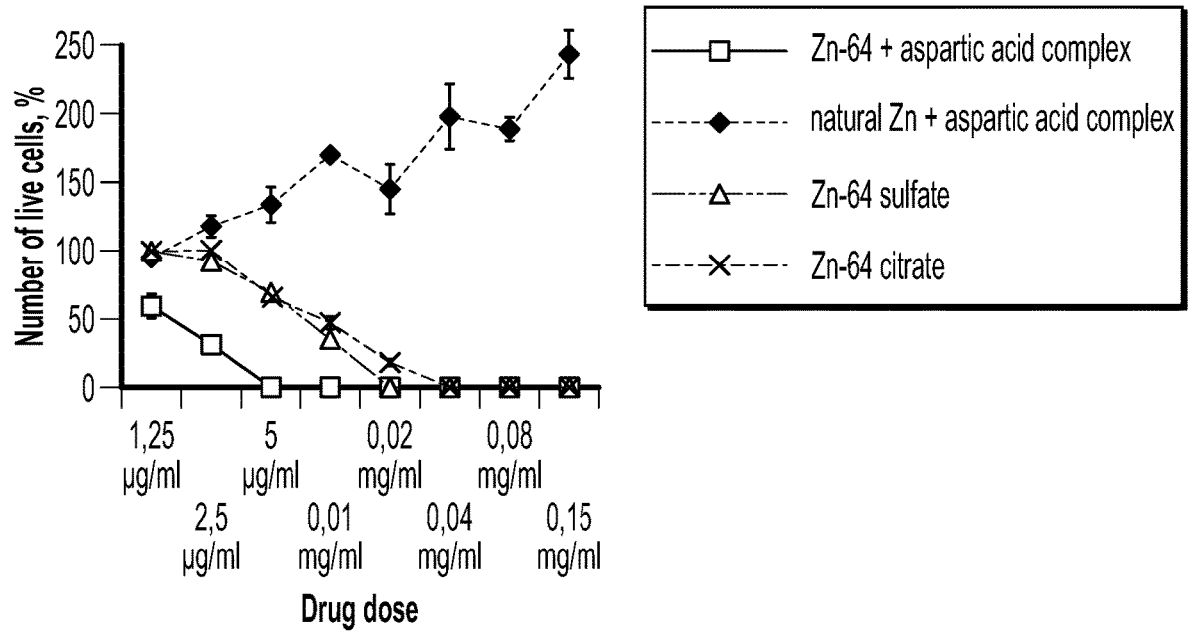
FIG. 2 is a graph showing cytotoxic/cytostatic action of natural zinc and Zn-64 compounds on Lewis lung carcinoma cells.
Figure 3:
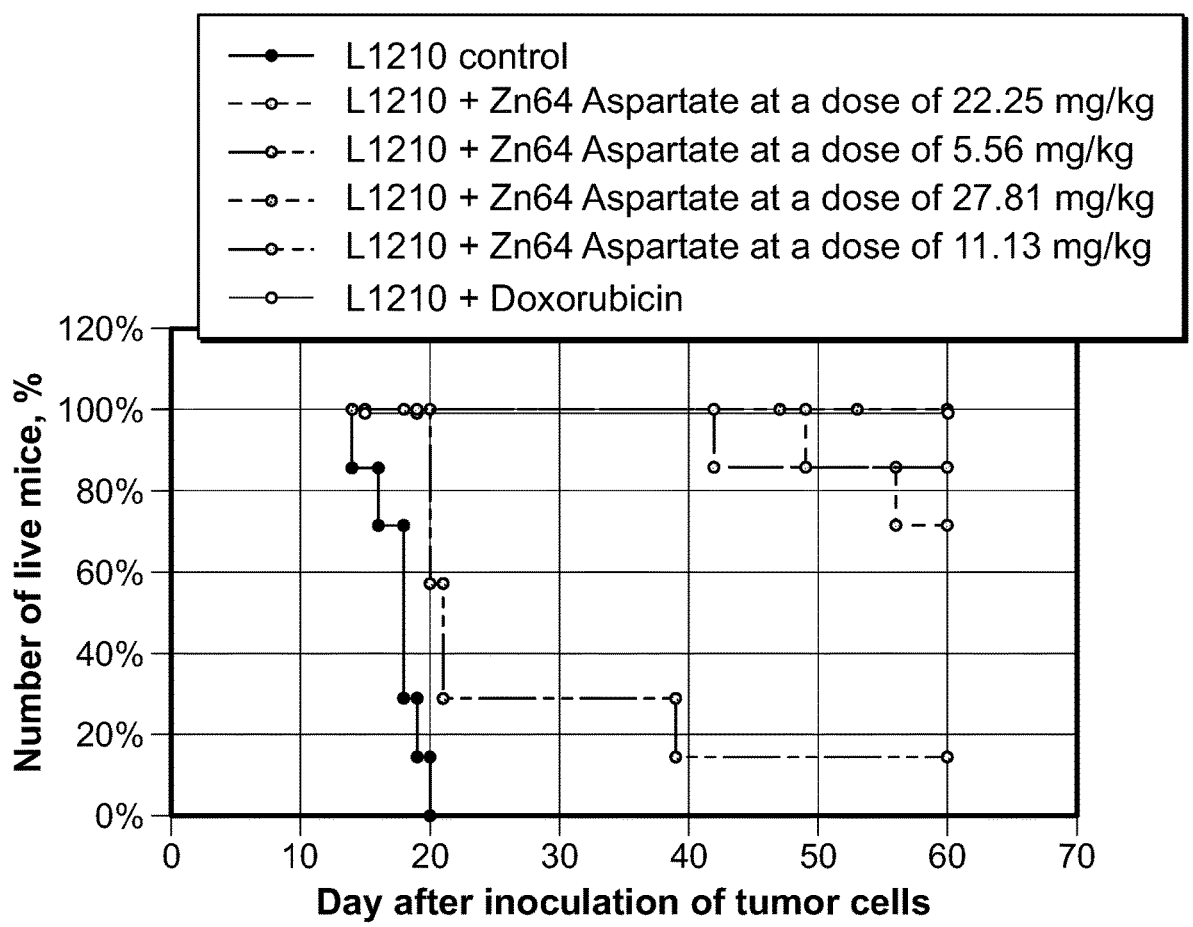
FIG. 3 is a graph showing treatment with Zn-64 (enrichment 99.2%) Inhibits Growth of L1210 Leukemia in mice.

As used herein, the word "a" or "plurality" before a noun represents one or more of the particular noun.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

All ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "5 to 10" or "5-10" should be considered to include the end points 5 and 10.

It is further to be understood that the feature or features of one embodiment may generally be applied to other embodiments, even though not specifically described or illustrated in such other embodiments, unless expressly prohibited by this disclosure or the nature of the relevant embodiments. Likewise, compositions and methods described herein can include any combination of features and/or steps described herein not inconsistent with the objectives of the present disclosure. Numerous modifications and/or adaptations of the compositions and methods described herein will be readily apparent to those skilled in the art without departing from the present subject matter.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

It is logical to assume that, in accordance with the "original design." human body should be made of light isotopes only. The problem is that food consists of chemical elements that are mostly mixtures of stable isotopes in proportions to their natural abundance. It means that the primary source of health problems is nutrition, which is in fact a mixture of poison and antidote. That is why people are destined for chronic and/or acute general and local degeneration.

Protein accounts for approximately 20 percent of a cell's total weight. Lodish H, Berk A, Zipursky S L, et al. Molecular Cell Biology. 4th edition. Section 1.2 New York: W. H. Freeman; 2000. All chemical elements coming into the body with food have isotope ratios in accordance with their well-known natural abundance. This exact ratio should be expected to be in the cell's cytoplasm. In case light isotopes are used in the protein's production, the isotope ratios in cytoplasm should be shifted in favor of heavy ones, leaving total average values per cell equal to the one of incoming into the cell.

Some cells produce proteins/polypeptides "for export." like hormones, cytokines or signaling molecules or breast milk components, for example. The very ability of the cell machinery to produce biomolecules "for export" depends on the materials delivered into the cell. Deficiency in timely supplies of light isotopes would lead to the enrichment of the cytoplasm with heavy isotopes. And use of these isotopes in protein production and inevitable degradation of the products quality: distortion of helices, tendency to the racemization of amino acids in proteins, their damaged conformation, unfolding and possibly aggregation and loss of function. Therefore, exactly these kinds of cells represent the best place for the onset of pathological changes in tissues and organs, including primary or metastatic cancers.

Proteins in the healthy living cell should contain only the lightest isotopes of hydrogen, oxygen, nitrogen, carbon essential chemical elements.

Potassium and rubidium, whether they bind to proteins or play other roles in a cell's life, are required to be in the form K-39 and Rb-85 isotopes.

Treating and preventing degenerative and infectious diseases require sufficient supply of light isotopes like Zn-64, K-39, Mg-24, K-39, or Fe-54, for example. The use of intravenous injections or oral pills with light isotopes compositions exceeding daily consumption dose by a factor of 2-4 for prophylactics of degenerative and infectious diseases can be extremely helpful. The efficacy of such approach depends on dose and drugs delivery time. The problem is that this approach cannot prevent heavy isotopes coming with food. As disclosed herein, the best solution of this problem is to consume isotope selective foods/agricultural products grown in soil fertilized with light isotopes of essential chemical elements. The lightest stable isotopes of essential chemical elements in therapeutic and preventive compounds with various salts and amino acids or biomolecules as vehicles should be used. The best vehicles are chemical compounds in plant foods.

It does not make sense to grow plants in soil for agricultural products with any currently known medical drugs: vaccines, antibiotics, inhibitors, activators, and even most sophisticated products like CAR-T cells as they simply decompose in the ground.

In contrast, salts and amino acids based compounds enriched with lightest isotopes of essential chemical elements can be used as a new type of nutrients or "fertilizers" in the process of agricultural production of various crops, fruits, and vegetables. They may serve as a part of hydroponic nutrient culture medium to produce sprouts or vegetables or to use fast growing plants with subsequent transformation into a compost enriched with lightest stable isotopes of essential chemical elements. This compost in turn can be used as a main component of the soil to grow plants on. Anti-viral and anti-bacterial action of light isotopes provide additional protection for the plants growing on this soil from bacteria and viruses. Products grown in this manner have unique prophylactic and therapeutic properties. These plants or trees would have the same properties as the Tree of Life. Thus, food becomes our medicine in accordance with the famous Hippocrates expression.

Daily consumption of isotope-selective food is the best way for promoting health and/or maintaining youthful homeostasis i.e. stability of human organism with simultaneous prevention from degenerative and infectious diseases. Daily consumption doses for essential chemical elements taken with foods are equal to the therapeutic doses determined during phase 1-2 clinical study in patients with metastatic solid tumors, autoimmune diseases, diabetes 1 and 2, obesity, aphasia, and Parkinson's disease.

Food for Promoting Health and/or Maintaining Homeostasis and Methods of Producing the Food In one aspect, this disclosure provides a method of producing a food product of a plant comprising growing the plant in fertilizer or compost comprising essential chemical elements enriched for lightest stable isotope or isotopes thereof; or foliar feeding the plant a solution comprising essential chemical elements enriched for lightest stable isotope or isotopes thereof; or growing the plant in hydroponics in a solution comprising essential chemical elements enriched for lightest stable isotope or isotopes thereof. In some embodiments, a food product of a plant is a vegetable or a fruit. In some embodiments, the fertilizer, compost, or solution fed to the plants (in which the plants are grown) comprises $^{64}Zn_e$. In some embodiments, the fertilizer, compost, or solution fed to the plants (in which the plants are grown) comprises $^{64}Zn_e$ sulfate, $^{64}Zn_e$ oxide or $^{64}Zn_e$ aspartate.

The term "$^{64}Zn_e$" is used herein to refer to $^{64}Zn$-enriched zinc. That is, zinc that is enriched for $^{64}Zn$ such that $^{64}Zn$ is enriched greater than its usual percentage in zinc in nature.

In another aspect, this disclosure provides a method of producing a livestock or a livestock product comprising growing the livestock by feeding the livestock food comprising essential chemical elements enriched for lightest stable isotope or isotopes thereof or a solution comprising essential chemical elements enriched for lightest stable isotope or isotopes thereof; or injecting the livestock intravenously a solution comprising essential chemical elements enriched for lightest stable isotope or isotopes thereof. In some embodiments, the livestock is injected intravenously a solution comprising an amount corresponding to the known daily consumption amount of said essential chemical elements. In some embodiments, the food or solution fed to the livestock comprises $^{64}Zn_e$. In some embodiments, the food or solution fed to the livestock comprises $^{64}Zn_e$ sulfate, $^{64}Zn_e$ oxide or $^{64}Zn_e$ aspartate. In some embodiments, the food or solution fed to the livestock comprises $^{64}Zn_e$ sulfate, $^{64}Zn_e$ oxide or $^{64}Zn_e$ aspartate.

In another aspect, this disclosure provides a method of producing an aquaculture product or a mariculture product comprising growing the aquaculture product or a mariculture product by feeding the aquaculture product or the mariculture product food or solution comprising essential chemical enriched for lightest stable isotope or isotopes thereof. In some embodiments, the food or solution fed to the aquaculture product or a mariculture product comprises $^{64}Zn_e$. In some embodiments the food or solution fed to the aquaculture product or a mariculture product comprises $^{64}Zn_e$ sulfate, $^{64}Zn_e$ oxide or $^{64}Zn_e$ aspartate. In some embodiments, the food or solution fed to the aquaculture product or a mariculture product comprises one or more salts, one or more metal oxides or one or more metal chelates with amino acids of said essential chemical elements.

In some embodiments, the livestock, aquaculture product or mariculture product is fed daily with food containing the lightest stable isotope or isotopes of essential chemical elements.

In another aspect, this disclosure provides a product of a plant, a livestock, a livestock product, an aquaculture product, or a mariculture product comprising essential chemical elements enriched for lightest stable isotope or isotopes thereof.

In another aspect, this disclosure provides a product of a plant made by a disclosed method.

In another aspect, this disclosure provides a livestock or a livestock product made by a disclosed method.

In another aspect, this disclosure provides an aquaculture product or a mariculture product made by a disclosed method.

In another aspect, this disclosure provides fertilizer or compost comprising essential chemical elements enriched for lightest stable isotope or isotopes thereof.

In some embodiments, the essential chemical elements are enriched for lightest stable isotope or isotopes thereof at higher than 85%, 90%, 95% or 99%.

In some embodiments, the essential chemical element(s) is(are) one or more of H, C, N, O, Zn, Fe, Mg, Si, Se, Rb, K, and Ca.

In some embodiments, the enriched stable isotope or isotopes of essential chemical elements is one or more of $^{39}K$, $^{24}Mg$, $^{64}Zn$, $^{85}Rb$, $^{28}Si$, $^{54}Fe$, $^{40}Ca$, $^{74}Se$.

In some embodiments, the enriched stable isotope or isotopes of essential chemical elements is one or more of $^{1}H$, $^{12}C$, $^{16}O$, $^{14}N$, $^{39}K$, $^{24}Mg$, $^{64}Zn$, $^{85}Rb$, $^{28}Si$, $^{54}Fe$, $^{92}Mo$, $^{74}Se$, $^{58}Ni$, $^{70}Ge$, $^{52}Cr$, $^{63}Cu$, and $^{50}V$.

The term "enriched" as referring to an isotope of an essential chemical element that is enriched such that it exists in the composition, formulation, compound, etc. at greater than its abundance normally found in nature.

In certain embodiments, zinc is enriched to be at least 80% $^{64}Zn_e$, at least 90% $^{64}Zn_e$, at least 95% $^{64}Zn_e$, or at least 99% $^{64}Zn_e$, for example, zinc that is 80% $^{64}Zn_e$, 85% $^{64}Zn_e$, 90% $^{64}Zn_e$, 95% $^{64}Zn_e$, 99% $^{64}Zn_e$, or 99.9% $^{64}Zn_e$.

In some embodiments, the $^{64}Zn_e$ is in a form of salt selected from the group consisting of aspartate, sulfate, and citrate. In some embodiments, the $^{64}Zn_e$ is in a form of $^{64}Zn_e$ aspartate with chemical formula of $C_4H_5O_4N^{64}Zn_e$ with 2 aspartic acid molecules.

In some embodiments, zinc aspartate has a chemical formula —$C_4H_5O_4N^{64}Zn_e$, with 2 aspartic acid molecules. In some embodiments, the structure of zinc aspartate is:

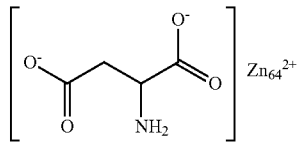

In another aspect, this disclosure provides food made from a disclosed product of a plant, food made from a disclosed livestock, food made from a disclosed livestock product, or food made from an aquaculture product or a mariculture product.

In another aspect, this disclosure provides a method of promoting health in a subject by feeding the subject one or more of food made from a disclosed product of a plant, food made from a disclosed livestock, food made from a disclosed livestock product, or food made from an aquaculture product or a mariculture product. In some embodiments, the food is cooked before feeding to the subject.

In another aspect, this disclosure provides a method of maintaining homeostasis in a subject by feeding the subject one or more of food made from a disclosed product of a plant, food made from a disclosed livestock, food made from a disclosed livestock product, or food made from an aquaculture product or a mariculture product. In some embodiments, the food is cooked before feeding to the subject.

The disclosed food may be consumed by a subject in any way a food is consumed and processed in any way food for consumption is processed.

As used herein, an agricultural product is a crop, livestock and livestock product, including but not limited to field crop, fruit, vegetable, cattle, sheep, hog, goat, horses, poultry, furbearing animals, milk, and eggs. An agricultural product includes plants and livestock and livestock products.

As used herein, a livestock product includes but is not limited to milk and eggs.

As used herein, food made from a livestock product includes but is not limited to milk, eggs, cream, yogurt, and cheese. Food made from a livestock product includes all dairy products.

As used herein, food made from a livestock includes but is not limited to meat (such as steak, roast, etc.), pâté, sausage, cured meats, and deli meats.

As used herein, a product of a plant includes but is not limited to field crop, fruit, and vegetable.

As used herein, food made from a product from a plant includes but is not limited to fruits, vegetables, plant oil, coffee, tea, cereal, grains, rice, pasta, potatoes, fruit or plant juice, beer, wine, wheat, oats, rye, barley, corn, triticale, millet, whisky and other alcoholic beverages, other beverages that contain fruit or plant matters, etc.

As used herein, the term "aquaculture" broadly refers to the cultivation of freshwater aquatic organisms in controlled aquatic environments for any commercial, recreational or public purpose. The breeding, rearing and harvesting of plants and animals takes place in all types of water environments including ponds, rivers, lakes, and man-made "closed" systems on land. Said cultivated freshwater aquatic organisms are "aquaculture products."

As used herein, food made from aquaculture products includes but is not limited to fish, clams, water mites, snails, eels, etc.

As used herein, the term "mariculture," or "marine aquaculture" broadly refers to the cultivation of marine aquatic organisms in controlled marine aquatic environments for any commercial, recreational or public purpose. The breeding, rearing and harvesting of plants and animals takes place in all types of water environments including oceans and man-made "closed" systems on land. Said cultivated marine aquatic organisms are "mariculture products" or "marine aquaculture products."

As used herein, food made from mariculture products includes but is not limited to fish, shrimps, crabs, lobsters, clams, mussels, jellyfish, squid, etc.

The term "hydroponics" refers to a method of growing plants, usually crops, without soil, by using solutions comprising nutrients.

The term 'foliar feeding" refers to a technique of feeding plants by applying a solution comprising liquid fertilizer directly to the leaves of the plants.

As used herein, a "subject" may be an animal subject or a plant subject. An animal subject includes a human subject or a non-human animal subject.

The disclosed food may be in any suitable form. The disclosed food may be consumed by first cooking the food or consumed raw.

As used herein, the term "light isotopes" refers to at least the following isotopes: $^{1}H$, $^{12}C$, $^{40}Ca$, $^{16}O$, $^{14}N$, $^{39}K$, $^{24}Mg$, $^{64}Zn$, $^{85}Rb$, $^{28}Si$, $^{54}Fe$, $^{92}Mo$, $^{74}Se$, $^{58}Ni$, $^{70}Ge$, $^{52}Cr$, $^{63}Cu$, and $^{50}V$.

Homeostasis and Health

Both infectious diseases and degenerative diseases remain health problems. Disruption to homeostasis for whatever reason needs to be addressed.

Homeostasis is the state of steady internal, physical, and chemical conditions maintained by living systems. Homeostasis is brought about by a natural resistance to change when already in the optimal conditions, and equilibrium is maintained by many regulatory mechanisms. Homeostasis is any self-regulating process by which biological systems tend to maintain stability while adjusting to conditions that are optimal for survival. The stability attained is actually a dynamic equilibrium, in which continuous change occurs yet relatively uniform conditions prevail.

Out of millions of species of bacteria and viruses, only few are harmful to humans. Centers for disease control and prevention indicates just 219 viruses and 18 antibiotic-resistant bacteria that may present real threat to humans.

Both vaccination and new antibiotics help ensure that the human organism is no longer a friendly place for hiding and proliferation of these harmful bacteria and viruses.

But the problem is that vaccines and antibiotics are virus or bacteria specific and therefore, are not equipped to protect humans from new infections and even from modified old ones. Mankind has to deal with new and possibly more dangerous pathogens continuously. It would be ideal if a mechanism exists for doing so.

In normal cells, proteins, including antibodies, are made from levorotatory amino acids and have structures with right-handed helices. But What if proteins on the surface of invading bacteria or viruses are unrecognizable to any antibodies produced by B cells? Bacteria or virus presenting proteins made of dextrorotatory amino acids would be invincible to the immune system. It does not matter how many random mutations in the antibody variable region genes will be produced, the most important change will never be possible to achieve—the change of the antibody chirality. Pathogen's proteins with wrong conformation due to the presence of right-handed amino acids would have significantly distorted helixes. The degree of distortion, which is proportional to the number of D-amino acids in it, may be a useful feature for the pathogen to counter antibodies and to vaccines.

For example, if the proteins of SARS-COV-2 have wrong conformation and/or partially unfolded, then antibodies would need to possess the same qualities and therefore, contain at least one or more D-amino acids. Such proteins may cause unfolded protein response resulting in severe local and systemic inflammation. Due to the presence of D-amino acids in their structure or in remains, antibodies, like virus itself, may act as catalysts, leading to the non-linear increase in the production yield of D-amino acids and proteins with wrong conformation in the process of autocatalytic amplification of chirality, similar to reactions described in Kenso Soai and Tsuncomi Kawasaki, Asymmetric autocatalysis with amplification of chirality, Springer-Verlag Berlin Heidelberg, published online, 27 Jul. 2007. It could be extremely dangerous as elevated levels of various D-amino acids, wrong conformation of proteins, unfolded and aggregated proteins are associated with at least 60 degenerative diseases if not all of them. R. W. Carrell, B. Gooptu Curr. Opin. *Struct. Biol.*, 8 (1998), pp. 799-809; Jacco J. A. J. Bastings, D-amino Acids in Health and Disease: A Focus on Cancer Nutrients 2019 September; 11(9): 2205.

Increasing concentration of D-amino acids in proteins has been reported in mild degeneration during "healthy" aging. This feature is widely used by forensic medicine for precise age determination. Ritz-Timme S, Collins M J. *Ageing Res Rev.* 2002 February; 1(1): 43-59; Noriko Fujii et al., *Biochim Biophys Acta Proteins Proteom.* 2018 July; 1866(7):840-847.

General and acute local aging/comorbidities and dangerous pathogens like SARS-COV-2 need and mutually complement each other. It explains why graphs describing incidents and mortality of degenerative diseases, which may be considered as an acute local aging process which may happen in the chronologically young organism, versus age are practically identical to Covid-19 ones.

The presence of right-handed amino acids and misfolded proteins (which means damaged negative feedback and disrupted homeostasis) may be a necessary condition for successful pathogenic virus penetration into organism and its further proliferation. But the virus may act as a catalyst of autocatalytic reactions with D-amino acids, resulting in transition of existed comorbidities into acute stage or causing new previously absent pathologies with possible fatal outcome. It depends on where and when autocatalytic reactions become non-linear with sharply increased yield leading to the clear manifestation of the symptoms of the pre-existed or new disease. In such manner infection of patient with obesity or diabetes 2 by SARS-COV-2 can result in complications related to cardiovascular system.

Covid-19 pandemic like no other case demonstrates the need for a strategy capable to address not only matters of life and death of a specific virus but also all types of degenerative pathologies plus aging related issues. In fact, charts of incidents of degenerative diseases/death rate of Covid-19 versus age speaks for themselves. The best solution is in shifting human body back in time, to the state characteristic for 20-25 years old person.

The ideal material for prevention and treatment of Covid-19 must combine several features and be able to:

Create an environment in live cells incompatible with the existence/survival of coronavirus;

Prevent and cure most challenging bacterial infections to deal with complications in respiratory tract/lungs, kidneys, and cardiovascular system;

Produce strong anti-inflammatory effect to prevent/eliminate cytokine storm;

Reactivate/rejuvenate immune and endocrine systems;

Restore healthy/youthful homeostasis to provide speedy and full recovery.

Methods of modern medicine are aimed at certain molecular signatures overexpressed in pathology affected cells or in pathogens. In some cases, they allow to reduce or temporarily eliminate symptoms and transform an acute form of the disease into a chronic one. At the same time protein targets being not overexpressed are still present in normal cells. That is why high side effects ultimately lead to the destruction of homeostasis. The so called "targeted therapy" may eliminate symptoms but leave the real cause of pathology intact.

The origin of degenerative diseases is unknown except for some inherited disorders connected to obvious mutations in DNA. Therefore, understanding pathogenesis is a master key for the prevention and treatment of both degenerative and infectious diseases. There are more than 200 degenerative disorders in the WHO list. Could it be that all of them have the same roots? In accordance with Georg W. F. Hegel, phenomenon is essential, and essence manifests itself in phenomena. In application to pathogenesis one and the same mechanism can be responsible for pathological changes but reveals itself in symptoms specific for each of 200 live cells. These symptoms then are used in the description of various pathologies.

It is not accidental that molecular signatures are proteins. Life was defined as existence of proteins for more than 150 years. In 2002 Stuart Kauffman defined life through the existence of proteins involved in autocatalytic reactions. Stuart Kauffman, Investigations. Oxford University Press, 19 Sep. 2002, 308p. Proteins are playing key role in providing stability of live cells, cell-to-cell interaction, and interconnection between vital systems of organism. They act as transmitters, receivers, and signals and thus protein's proper composition and conformation are crucial in the functioning of the most important component of any stable system—negative feedback or homeostasis in live objects. Wrong conformation, let alone unfolding of proteins with follow up aggregation, inevitable leads to avalanche-like crush of negative feedback and hence, the stability of cells, tissues, organs, and destruction of the organism. Disruption to homeostasis follows.

In quantum mechanics of the atom, an energy level is called degenerate if it corresponds to two or more different states of a quantum system. Amino acid with opposite chirality present in the one and the same protein is a good analog of degenerate state for biomolecule. The problem is that a mixture of L and D-amino acids cannot form helices at all. Presence of even one D-amino acid in the protein will always lead to distortion of the helices.

The important question is what comes first: the distortion of helices and change of amino acid chirality as a result, or incorporation of D-amino acid during translation process which leads to the distortion of the helices and conformation of a protein. In both cases such a degenerate state of proteins would cause degeneration or gradual deterioration of the human organism. Timing/speed of degeneration is defined by parameters of relevant autocatalytic reactions responsible for biomolecules synthesis in a living cell. Based on the well-established direct proportionality between concentration of D-amino acids in long living proteins and age, it is logical to suggest that distortion of the protein helices happens first. On the other hand, what could be better stabilizer of said distortion than chirality change of at least one amino acid.

Consider wild type proteins, in which case any structural defects cannot be attributed to DNA mutations. Amino acids in wild type proteins are the simplest "indivisible" particles of proteins and polypeptides. What is more fundamental than amino acids in the structure of proteins? Only chemical elements. Can chemical elements contribute to the degeneration of biomolecules? In fact, there are only 26 monoisotopic elements in the periodic system. The rest have one or more stable isotopes, and, in this sense, stable chemical elements are degenerate. According to physics and chemistry textbooks, isotope effects observed in relatively simple inorganic and organic compounds are negligible and therefore, substitution of one isotope on another of the same chemical element at no circumstances could affect structure of molecules.

However, in the past 10 years it was discovered that isotope substitutions of hydrogen (H/D) (Kawasaki T et al., Chem. Commun. 2009, 4396-4398), carbon ($^{12}C/^{13}C$) (Kawasaki T. et al., Science 2009, 324, 492-495), oxygen ($^{16}O/^{18}O$) (Kawasaki T. et al., Angew. Chem. Int. Ed. 2011, 50, 8131-8133; Angew. Chem. 2011, 123, 8281-8283) and nitrogen ($^{14}N/^{15}N$) (Dr. Arimasa Matsumoto et al., Angew Chem Int Ed Engl. 2016 Dec. 5; 55(49): 15246-15249) act as chiral initiators for asymmetric autocatalysis leading to the production of compounds with mirror image chirality. Isotope induced chirality was discussed from the viewpoint of symmetry braking and believed to be a stochastic process. Avalos M et al., Chem. Commun. 2000, 887-892.

All proteins contain L-amino acids and that cannot be random, pointing to the necessity of reconsidering the possible role of atomic nucleus in the formation of chiral biomolecules and solenoids/helices in the structure of protein and DNA.

In this regard, the results of the investigation of complex dust plasmas under microgravity conditions on the International Space Station are extremely interesting. V N Tsytovich et al., New Journal of Physics 9 (2007) 263; H M Thomas et al., New Journal of Physics, Volume 10, March 2008. They have detected " . . . the formation of a helical dust structures, after they are formed, resembles features like those of DNA. They can transfer information from one helical structure to another via the dust convective cells surrounding any bifurcation of the helical structure." V N Tsytovich et al., New Journal of Physics 9 (2007) 263.

These DNA-like structures are made of plastic or $CeO_2$ particles formed in the field produced by two interconnected generators. One for plasma production and another for the modulation of electric field. At the same time, the very fact of the formation of solenoidal/helical structures indicates that not electric but electromagnetic fields in competition of modes regime are involved in this process. It makes sense to consider the role of the competition of modes produced by electron subsystem and nucleus of atoms in the formation of chemical bonds and helical structures of proteins and DNA.

From the practical point of view:
Degenerative disorders may be associated with wrong conformation of proteins.
Wrong conformation of protein may be accommodated by the formation of one or more D-amino acids.
Both distortion of helixes and mirror-image amino acids may be isotope-induced in result of the substitution of lightest isotopes by heavy ones of the same chemical element.

Isotope-induced changes in the symmetry of biomolecules can be caused not only by such basic elements as hydrogen, carbon, oxygen, and nitrogen but also by essential chemical elements.

Isotope-induced chirality and its amplification in asymmetric autocatalysis could go in both directions. It means that reverse isotope selective autocatalytic reactions may lead to the isotope separation in live cells.

If true, isotope separation effect could be the most critical feature which defines the fate of live cells and makes all the difference between normal and pathology affected cells and tissues, young and senescent cells, and at the end—between life and death.

Isotope composition of biomolecules should be a decisive factor for stability/homeostasis in both healthy/young organism and efficient pathogens (whether it is bacteria or virus).

The sources of our energy and construction material of human body are not inhibitors and activators, antibodies, and CAR-T cells but degenerate chemical elements which are in fact a mixture of various stable isotopes.

Hippocrates words "Let food be thy medicine and medicine be thy food" could appear to be prophetic.

Speaking of non-live matter, isotope ratios for all chemical elements are practically one and the same and not only on our planet but in all corners of the Universe. Deviations from natural abundance in the same chemical element exist but on the level of parts per million only. Inorganic materials, on the other hand, are quite different from biomolecules. They do not have a hierarchical structure with helical/solenoidal component on the top level. Their crystalline structure can be well described based on Coulombic interaction so that there is no reason to expect any significant effects related to nucleus composition including isotope induced changes of symmetry.

If so, then, in live matter an opposite situation should be found. Taking into consideration the amplification role played by autocatalysis, dramatic difference should be found in isotope composition of healthy and most important cells and tissues on the one side, and pathology affected cells and tissues, and probably pathogens as well, on another one. It would require human cells or organs to have isotope separation ability. As there is no place for centrifuges, plasma or electromagnetic separation machinery in the human body, the hypothesis about involvement of asymmetric catalysis in such process seems plausible.

The most aggressive degenerative disease is cancer. Then, cancer cells and tissues and especially metastases are likely to be enriched with heavy isotopes of all relevant elements. The problem is that heavy isotope ratios of carbon, hydrogen, nitrogen, and oxygen are exceedingly small and are equal correspondently 1.10; 0.02; 0.4; and 0.24%. Therefore, even if they increase 2-3 times, the difference is difficult to detect. That is why mostly essential chemical elements are looked at. The additional intuitive argument is that primary tumors and metastases location closely coincide with the map of endocrine glands and hormones producing cells. Translated from Greek, the word "endocrine" means "sifter inside". Sifter is a perfect word to describe the essence of the separation of lightest isotopes from the rest of them.

TABLE 1

Isotope ratios in cancer cells and tissues

| Element | Isotope | Natural Abundance % | Leukemia Lymphocytes Avg. % | Intestinal Tumor Avg. % | Metastasis of Intestinal Tumor Avg. % | Tissue Around Metastasis of Intestinal Tumor Avg. % |
|---|---|---|---|---|---|---|
| Zn | Zn64 | 48.60 | 45.59 ± 0.66 | 46.49 ± 0.35 | 40.59 ± 0.15 | 55.62 ± 2.51 |
|  | Zn66 | 27.90 | 25.44 ± 0.7 | 24.66 ± 2.64 | 25.5 ± 0.28 | 25.22 ± 1.84 |
|  | Zn67 | 4.10 | 3.85 ± 0.04 | 4.82 ± 0.1 | 3.85 ± 0.04 | 3.93 ± 1.0 |
|  | Zn68 | 18.80 | 23.77 ± 1.27 | 20.42 ± 0.14 | 23.77 ± 1.27 | 14.63 ± 1.24 |
|  | Zn70 | 0.60 | 1.42 ± 0.21 | 3.63 ± 0.2 | 6.29 ± 0.2 | 0.60 |
| Fe | Fe54 | 5.80 | 4.07 ± 0.46 | 4.44 ± 1.25 | 3.07 ± 0.02 | 6.43 ± 0.21 |
|  | Fe56 | 91.72 | 91.4 ± 0.24 | 91.29 ± 0.38 | 91.4 ± 0.24 | 91.13 ± 0.19 |
|  | Fe57 | 2.20 | 4.25 ± 0.61 | 2.16 ± 0.12 | 5.25 ± 0.3 | 2.16 ± 0.06 |
|  | Fe58 | 0.28 | 0.28 | 2.11 ± 0.03 | 0.28 | 0.28 |
| Mg | Mg24 | 78.99 | 76.53 ± 0.46 | 78.47 ± 0.24 | 74.19 ± 0.88 | 80.95 ± 0.6 |
|  | Mg25 | 10.00 | 7.57 ± 0.19 | 6.47 ± 0.3 | 9.57 ± 0.18 | 9.57 ± 0.44 |
|  | Mg26 | 11.01 | 15.93 ± 0.5 | 15.06 ± 0.76 | 16.23 ± 0.29 | 9.39 ± 0.64 |
| Si | Si28 | 92.23 | 89.84 ± 0.57 | 90.84 ± 0.39 | 87.71 ± 0.84 | 92.73 ± 0.1 |
|  | Si29 | 4.67 | 4.04 ± 0.25 | 4.49 ± 0.24 | 3.38 ± 0.6 | 4.51 ± 0.1 |
|  | Si30 | 3.10 | 6.12 ± 0.17 | 4.67 ± 0.3 | 8.91 ± 0.71 | 2.76 ± 0.09 |
| Se | Se74 | 0.90 | 0.90 | 0.90 | 0.90 | 0.90 |
|  | Se76 | 9.00 | 4.41 ± 0.23 | 7.73 ± 0.58 | 3.51 ± 0.37 | 10.84 ± 2.32 |
|  | Se77 | 7.60 | 8.67 ± 0.7 | 3.33 ± 0.21 | 7.33 ± 0.37 | 7.97 ± 0.85 |
|  | Se78 | 23.60 | 25.89 ± 2.64 | 25.98 ± 1.72 | 25.89 ± 2.64 | 22.32 ± 1.53 |
|  | Se80 | 49.70 | 49.70 | 50.61 ± 0.33 | 50.13 ± 1.28 | 49.70 |
|  | Se82 | 9.20 | 10.42 ± 0.55 | 11.46 ± 0.16 | 12.25 ± 0.61 | 8.27 ± 0.88 |
| Rb | Rb85 | 72.16 | 68.19 ± 1.33 | 70.45 ± 0.22 | 65.19 ± 0.23 | 73.7 ± 0.38 |
|  | Rb87 | 27.84 | 31.81 ± 0.7 | 29.55 ± 0.22 | 34.81 ± 0.18 | 26.3 ± 0.38 |

If isotopes are separated, and light ones are used in the production of hormones, which are very important polypeptides and proteins in the body, then, the byproduct of such production process—heavy isotopes—should be accumulated nearby production sites and attract loose single cancer cells and other pathogens being their feeding ground. It plays well with the role of comorbidities in Covid-19 infection and death rate also.

TABLE 2

Isotope ratios of normal cells, breast milk and sperm

| Element | Isotope | Natural Abundance % | Sperm Avg. % | Breast Milk Avg. % | Healthy Lymphocytes Avg. % | Erythrocytes Avg. % | Thrombocytes Avg. % | PL of Healthy Blood Avg. % |
|---|---|---|---|---|---|---|---|---|
| Zn | Zn64 | 48.60 | 63.34 ± 0.89 | 53.58 ± 0.22 | 58.83 ± 0.79 | 56.64 ± 1.33 | 55.00 ± 1.11 | 59.1 ± 0.46 |
|  | Zn66 | 27.90 | 28.07 ± 0.51 | 27.52 ± 0.34 | 30.88 ± 1.39 | 27.6 ± 0.81 | 31.38 ± 5.56 | 27.62 ± 1.51 |
|  | Zn67 | 4.10 | 4.25 ± 0.26 | 3.89 ± 0.08 | 3.74 ± 1.33 | 3.66 ± 0.24 | 4.25 ± 1.56 | 3.71 ± 0.98 |
|  | Zn68 | 18.80 | 3.81 ± 0.39 | 14.96 ± 0.56 | 5.95 ± 0.29 | 11.99 ± 0.01 | 8.77 ± 0.45 | 8.97 ± 0.63 |
|  | Zn70 | 0.60 | 0.57 ± 0.1 | 0.05 ± 0.03 | 0.60 | 0.11 ± 0.03 | 0.60 | 0.60 |
| Fe | Fe54 | 5.80 | 11.64 ± 0.57 | 5.99 ± 0.1 | 1.17 ± 0.68 | 10.4 ± 0.49 | 8.68 ± 0.23 | 6.14 ± 0.17 |
|  | Fe56 | 91.72 | 87.78 ± 1.15 | 93.66 ± 0.08 | 87.55 ± 0.77 | 88.64 ± 0.71 | 90.89 ± 0.38 | 93.6 ± 0.22 |
|  | Fe57 | 2.20 | 0.26 ± 0.03 | 0.07 ± 0.03 | 0.98 ± 0.51 | 0.93 ± 0.03 | 0.15 ± 0.14 | 0.04 ± 0.03 |
|  | Fe58 | 0.28 | 0.28 | 0.28 | 0.28 | 0.01 | 0.28 | 0.22 |
| Mg | Mg24 | 78.99 | 83.04 ± 1.15 | 83.81 ± 0.97 | 83.65 ± 0.89 | 85.72 ± 0.44 | 82.1 ± 1.39 | 83.99 ± 0.59 |
|  | Mg25 | 10.00 | 10.72 ± 0.21 | 11.13 ± 0.33 | 9.57 ± 0.87 | 8.92 ± 0.44 | 9.57 ± 1.32 | 9.52 ± 0.46 |
|  | Mg26 | 11.01 | 6.38 ± 0.8 | 5.06 ± 0.04 | 6.77 ± 0.6 | 5.36 ± 0.86 | 7.45 ± 1.18 | 6.49 ± 0.25 |
| Si | Si28 | 92.23 | — | 93.41 ± 0.22 | 96.48 ± 0.71 | 93.66 ± 0.31 | 92.07 ± 0.63 | 94.64 ± 0.76 |
|  | Si29 | 4.67 | — | 4.78 ± 0.17 | 0.85 ± 0.3 | 3.49 ± 0.29 | 4.77 ± 0.44 | 4.85 ± 0.34 |
|  | Si30 | 3.10 | — | 1.81 ± 0.77 | 2.67 ± 0.15 | 2.85 ± 0.48 | 3.16 ± 0.33 | 0.51 ± 0.27 |
| Se | Se74 | 0.90 | — | 0.90 | 2.73 ± 0.81 | 3.62 ± 0.42 | 0.90 | 0.90 |
|  | Se76 | 9.00 | — | 14.35 ± 0.69 | 15.29 ± 1.28 | 11.67 ± 0.46 | 14.9 ± 0.8 | 16.29 ± 1.04 |
|  | Se77 | 7.60 | — | 6.37 ± 1.14 | 8.29 ± 0.98 | 8.13 ± 0.66 | 7.54 ± 0.76 | 6.79 ± 1.14 |
|  | Se78 | 23.60 | — | 24.49 ± 1.27 | 23.27 ± 1.18 | 24.81 ± 1.15 | 20.39 ± 0.24 | 23.65 ± 1.72 |
|  | Se80 | 49.70 | — | 46.70 | 49.70 | 44.14 ± 0.83 | 49.70 | 44.53 |
|  | Se82 | 9.20 | — | 7.19 ± 0.93 | 0.72 ± 0.16 | 7.63 ± 1.02 | 6.57 ± 1.09 | 7.83 ± 1.11 |
| Rb | Rb85 | 72.16 | 90.95 ± 0.78 | 77.01 ± 0.89 | 92.12 ± 0.82 | 77.47 ± 0.28 | 91.53 ± 2.02 | 77.16 ± 0.18 |
|  | Rb87 | 27.84 | 9.04 ± 0.03 | 22.99 ± 0.89 | 7.88 ± 0.82 | 22.53 ± 0.49 | 8.47 ± 2.02 | 22.84 ± 0.56 |

TABLE 3

Isotope ratios in mice primary M16 melanoma Measurements

| Isotope | 1 | 2 | 3 | 4 | 5 | 6 | Average Value | Natural Abundance |
|---|---|---|---|---|---|---|---|---|
| Mg24 | 74.93 | 75.07 | 75.02 | 79.91 | 73.40 | 75.80 | 75.69 | 78.99 |
| Mg25 | 10.98 | 10.63 | 11.15 | 9.16 | 10.25 | 8.54 | 10.12 | 10.00 |
| Mg26 | 13.09 | 14.30 | 13.78 | 14.66 | 14.43 | 14.87 | 14.19 | 11.01 |
| Si28 | 91.92 | 90.91 | 94.12 | 93.48 | 91.15 | 90.32 | 91.98 | 92.23 |
| Si29 | 5.56 | 6.06 | 3.53 | 3.62 | 5.51 | 6.45 | 5.12 | 4.67 |
| Si30 | 2.53 | 3.03 | 2.35 | 2.90 | 3.34 | 3.23 | 2.90 | 3.10 |
| Cl35 | 74.66 | 75.52 | 77.27 | 74.94 | 76.10 | 75.34 | 75.64 | 75.77 |
| Cl37 | 25.34 | 24.48 | 22.73 | 25.06 | 23.90 | 24.66 | 24.36 | 24.23 |
| Fe54 | 2.84 | 2.27 | 2.95 | 2.31 | 2.60 | 2.74 | 2.62 | 5.80 |
| Fe56 | 91.86 | 91.61 | 91.47 | 91.52 | 91.33 | 91.81 | 91.60 | 91.72 |
| Fe57 | 4.01 | 5.84 | 5.20 | 5.90 | 5.90 | 6.17 | 5.50 | 2.20 |
| Fe58 | 0.28 | 0.28 | 0.28 | 0.28 | 0.28 | 0.28 | 0.28 | 0.28 |
| Zn64 | 44.32 | 44.21 | 43.36 | 43.73 | 43.79 | 43.32 | 43.79 | 48.60 |
| Zn66 | 26.56 | 27.88 | 29.55 | 30.05 | 27.61 | 27.13 | 28.13 | 27.90 |
| Zn67 | 6.55 | 6.26 | 7.37 | 7.62 | 7.52 | 7.84 | 7.20 | 4.10 |
| Zn68 | 21.97 | 21.04 | 21.12 | 20.49 | 20.57 | 20.11 | 20.88 | 18.80 |
| Zn70 | 0.60 | 0.60 | 0.60 | 0.60 | 0.60 | 0.60 | 0.60 | 0.60 |
| Rb85 | 55.00 | 47.22 | 42.42 | 34.48 | 33.33 | 35.14 | 41.27 | 72.16 |
| Rb87 | 45.00 | 52.78 | 57.58 | 65.52 | 66.67 | 64.86 | 58.73 | 27.84 |

Mass spectrometry data (Tables 1-3) obtained using various healthy and cancer cells and tissues not only supports this model but in addition demonstrates that heavy isotope ratios of all essential chemical elements are proportional to the degree of pathological changes (much higher in metastases then in primary tumors). There is an expressive difference between light and heavy isotopes ratios of the same chemical elements found in healthy and leukemic lymphocytes. Lymphocytes are immune system cells. The data suggest that efficacy of T cells, B cells and natural killer cells is defined by isotope ratios of essential chemical elements, which is in complete agreement with this model of pathogenesis. The difference between isotope ratios of normal and cancer cells is so dramatic that makes it difficult to believe in the possibility of a successful cancer treatment or cure without addressing it.

The study of essential chemical elements and their isotope ratios in various cells and hormones provides strong indications that the red bone marrow, organs, and cells producing signaling molecules and hormones can separate isotopes. This data justifies enrichment of critical cells and molecules with light isotopes, to ensure that polypeptides and proteins have the perfect conformation.

According to this model, pathology cannot progress absent heavy isotopes. To fight diseases, the "isotope ratios" can be changed of essential chemical elements in favor of atoms that have an equal number of protons and neutrons or minimum excess of neutrons over protons. The ideal therapeutic composition should include a mixture of the lightest isotopes of essential chemical elements in the amounts proportional to the correspondent daily consumption dose. This approach should be sufficient to correct the structure of the metalloproteins but not of all proteins. To make sure that all proteins are produced without mistakes all stages of their synthesis and assembly must be addressed; these are transcription, translation, and posttranslational modification.

Living cells use several mechanisms to repair damaged DNA and mitigate problems related to mutant and misfolded proteins. There are several repair mechanisms involving other proteins, which must also be functional and responsible for facilitating the correct conformational assembly and catalytic activity for each protein which maintains homeostasis within the human body.

In general, all proteins, including transcription factors, are produced in ribosomes. Ribosomes synthesize peptides from amino acids according to the instruction from messenger RNAs and are one of the most important molecular machines in live cells. The quality of ribosomes defines the quality of proteins. A ribosome is composed of a large subunit and a small subunit, together consisting of three to four ribosomal RNAs (rRNAs) and dozens of ribosomal proteins (r-proteins). Common features in ribosomal proteins are zinc finger motifs, which have been associated with the proteins of both subunits of the ribosomes. Ribosomal proteins play a major role as RNA-binding proteins. Success of the translation process hinges on proper binding of zinc finger proteins and therefore, on their conformation. The average lifetime of ribosomes is 4-6 minutes. They are rapidly produced in autocatalytic reactions. Autocatalytic reactions may amplify the yield of proteins with the wrong conformation induced by isotope substitution of heavy isotopes. The probability of these events is quite low for non-metalloproteins, as their atoms light isotopes ratio is close to 100%.

The situation is completely different in case of zinc fingers. Isotope ratio for the stable isotope with minimum excess of neutrons over protons —Zn-64 is just 48.60%. Therefore, the probability of substitution by heavier isotopes is exceedingly high. The situation could be negatively impacted by asymmetric autocatalysis. It renders the probability of the resulting mistranslation in all produced proteins high.

Zinc is recognized as one of the most essential chemical elements in the human body. Numerous scientific articles have documented the effect of excess or lack of zinc on human health. The influence of zinc is mentioned in relation to at least 60 diseases. However, the most important issue is which precise zinc of the five stable isotopes is not addressed in scientific literature. It is this issue that is fundamental to the proper operation of the ribosome and therefore, for synthesis of all proteins with the correct conformation.

In immune system cells produced by the red bone marrow, as well as in signaling molecules produced by the endocrine system, the isotope ratio of light isotope Zn-64 significantly exceeds natural abundance. Conversely, a much higher concentration of heavy zinc isotopes is observed in the cells of pathology affected tissues. A short-term or long-term increase in the concentration of light zinc isotopes in the cytoplasm of cells will ensure their access to the ribosomes. This will lead to a sharp increase in the proportion of proteins with the correct conformation produced by ribosomes. The goal is to replace all damaged/old biomolecules, including all receptors and signaling molecules with new/young ones made of predominantly light isotopes.

Therapeutic compositions that increase the isotope ratio of Zn-64 in the cytoplasm of living cells is a completely new family of drugs with general effect. Such drugs create conditions incompatible with life of cells affected by the most serious pathologies, such as cancer, for example.

An important feature of such drugs is that their efficacy should grow with increased aggressiveness of the disease, such as stage IV cancers.

With the application of the correct protocol for the use of the drug, the recovery from degenerative diseases and restoration of homeostasis typical for a young and healthy organism are expected to be ensured. The expected outcome should include renewed immune and endocrine systems and rejuvenated living cells.

The conclusion about the influence of the isotopic composition of chemical elements on the homeostasis of biological systems suggests a paradigm shift in the understanding of the nature of pathogenesis.

Use of Formulation Comprising $^{64}$Zn as Therapeutic Agent $^{64}$Zn, the lightest epitope of Zinc, has been found to be useful in treating and preventing a number of diseases and conditions, as detailed in this section. See, e.g., U.S. Pat. Nos. 10,799,530 and 10,933,091. The studies summarized in this section use $^{64}$Zn or $^{64}$Zn$_e$-based compositions administered to an animal subject by, for example, injection, but not as food to an animal subject.

In some of the studies described in this section, drug delivery was done through I.V. infusions over a period of 1-1.5 hours. The lifetime of ribosome in which all proteins are assembled is 6 minutes. To make sure that ribosome's zinc fingers are perfect due to the presence of the lightest isotope of zinc —Zn-64 it would be much better to inject a subject around the clock. Delivery of the essential chemical elements lightest isotopes with food is far more practical as food is digested during day and night.

Anti-Cancer Mechanism of Action of $^{64}$Zn—Aspartate, Apoptosis, Ex Vivo/In Vitro An illustrative example of the opposite effect of natural zinc and a stable isotope Zn-64 on the proliferation of cancer cells is summarized below.

Effects of $^{64}$Zn on the expression of EMP-associated cell adhesion molecules in Burkitt lymphoma cells (Namalwa cell line) and human acute myeloid leukemia (HL-60 cell line), renal carcinoma in rats (strain RA), human breast cancer cells (MCF-7 cell line), human non-small cell lung cancer (A-549 cell line), and human colon carcinoma (COLO 205 cell line) were studied using immunocytochemical analysis.

It was found that $^{64}$Zn at a concentration of 20 µg/ml did not have any effect on the expression of E-cadherin, N-cadherin and CD44 in A-549 and MCF-7 cells. COLO 205 cells cultured in the presence of $^{64}$Zn (20 µg/ml) showed a statistically significant increase in the E-cadherin expression—by 62.1% compared with the control. However, the test substance did not have any effect on the N-cadherin and CD44 expression in COLO 205 cells. It should be noted that $^{64}$Zn had the greatest effect on the expression of E-cadherin (an epithelial cell marker) in COLO 205 cells with dominating mesenchymal characteristics. The obtained results suggest that cells with a more malignant mesenchymal phenotype are more sensitive to the effects of the test substance, and, according to literature data, an increase in the E-cadherin expression in tumor cells is associated with inhibition of malignant properties of cells.

Analysis of the Slug transcription factor expression in tumor cells cultured in the presence of $^{64}$Zn at a concentration of 20 µg/ml showed: 1) absence of any changes in SLUG expression in MCF-7 cells with an epithelial phenotype; 2) a statistically significant increase in nuclear and decrease in cytoplasmic Slug expression (re-localization)—by 29.4% and 46.7%, respectively, vs. control—in A-549 cells with a mixed phenotype; 3) a statistically significant increase in the nuclear and cytoplasmic Slug expression—by 11 and 2.7 times, respectively, vs. control—in COLO 205 cells with a mesenchymal phenotype.

Reduced cytoplasmic Slug expression in A-549 cells may indicate inhibition of their malignancy. It is known that Slug (a zinc finger protein) is a direct E-cadherin repressor and an increase in the expression of this transcription factor causes a decrease in the E-cadherin expression. However, COLO 205 cells exposed to $^{64}$Zn showed an increase in the Slug expression level against the background of increased E-cadherin expression. In addition, it is known that stable overexpression of Slug is accompanied by an increase in the sensitivity of cancer cells to anticancer drugs that target microtubules of the cell cytoskeleton and tubulin. Thus, it can be assumed that an increase in the Slug expression in COLO 205 cells with a mesenchymal phenotype does not lead to an increase in their malignancy but increases their sensitivity to the action of cytostatic agents.

A second study was done on mouse model of lymphocytic leukemia, strain of L1210 leukemia cells, mouse melanoma model (MM-4 cell line derived from mouse melanoma cells of strain B16). Typical results are below.

In vitro analysis of viability of MM-4 mouse melanoma cells after they were cultured in the presence of Zn64 Aspartate showed that the test substance at the concentration of 16.69 μg/ml suppressed proliferation of MM-4 cells by 22.2% (IC20) compared with the control. An increase in the Zn64 Aspartate dose to 25.03 μg/ml led to reduction in the number of live melanoma cells by 49.2% (IC50) compared with the control.

The effect of Zn64 Aspartate on the expression of anti-apoptotic protein Bcl-2 and pro-apoptotic proteins Bax and p53 (monoclonal antibodies against p53 (Y-5 clone) bind only to mutant p53 proteins, and p53 (DO-7 clone) bind to both mutant p53 and wild-type proteins) was analyzed using immunocytochemistry. It was shown that culture of MM-4 cells in the presence of Zn64 Aspartate at the dose of 16.69 μg/ml caused a statistically significant decrease in the expression of Bcl-2 (by 69.5% vs. control) but did not have any effect on the expression of pro-apoptotic proteins Bax and p53. An increase in the concentration of Zn64 Aspartate in the culture medium to 25.03 μg/ml statistically significantly increased the expression levels of Bax and p53 (DO-7 clone) by 8.9 and 9.5 times, respectively, compared with the control. It should be noted that Zn64 Aspartate used at this concentration causes a significant increase in expression of p53 (DO-7 clone) in MM-4 cells but does not influence the expression level of p53 (Y-5 clone).

The results suggest that Zn64 Aspartate activates expression of wild type p53 protein in MM-4 cells. At the same time, the test substance does not have any effect on the expression of anti-apoptotic protein Bcl-2. Thus, a significant increase in the expression of pro-apoptotic proteins Bax and p53 may indicate the activation of apoptosis in MM-4 mouse melanoma cells as a result of their treatment with Zn64 Aspartate at a concentration that should not lower than IC50.

According to literature data, metalloproteinases 2 and 9 (MMPs) are particularly important elements of the tumor microenvironment since they take an active part in the regulation of metabolism and cell cycle in tumor cells. It is also known that a decrease in the activities of MMP-9 and MMP-2 in tumor tissue is accompanied by suppression of tumorigenicity and tumor invasiveness. Analysis of the activities of latent (pro-MMP-2 and pro-MMP-9) and active forms (MMP-2 and MMP-9) of metalloproteinases in MM-4 cells after their treatment with Zn64 Aspartate showed a significant and dose-dependent suppression of the activities of these gelatinases.

Thus, treatment of MM-4 cells with the test substance (Zn64 Aspartate) at the concentration of 16.69 μg/ml caused a statistically significant decrease in the activities of latent pro-MMP-2 and pro-MMP-9 forms (by 76.5% and 61.2%, respectively, compared with the control), as well as of active MMP-2 and MMP-9 forms of metalloproteinases (by 66.8% and 23.8%, respectively, compared with the control). Culture of melanoma cells at the presence of Zn64 Aspartate at the concentration of 25.03 μg/ml was accompanied by statistically significant suppression of the activities of MMP-2 and MMP-9 by 76% and 18.8%, respectively, compared with the control. The findings suggest that the test substance not only suppresses proliferation of MM-4 cells, but it may also reduce their malignancy.

Modern methods of medicine are aimed at inhibiting certain receptors and signaling pathways in diseased cells. This inevitably leads to the activation of a destructive positive feedback loop in both healthy and pathology-affected cells, with all the ensuing consequences.

The disclosed technology aims to restore healthy and youthful homeostasis in adult and old organisms with no effect on the young ones unless correction is required. This target is achieved by rejuvenation of immune and endocrine systems and adding Geno-protective ability to live cells.

Effect of the Zn64 Aspartate on Obesity and Type 1 & 2 Diabetes In Vivo

The administration of Zn-64 Asp to animals on a high-fat diet result in:

Decrease in their body mass index

Reduction of weight and the amount of food consumed compared to the untreated animals Improvement of the lipid metabolism in the body of animals on a high-fat diet.

Increase of the cross-sectional surface area of the islets of Langerhans by 43% compared with the obesity group in which a cross-sectional surface area of the islets of Langerhans was significantly reduced (by 60%)

Disappearance of fatty degeneration in DIO (DIO—diet induced obesity) group, without a noticeable effect on exocrine cells in rats fed a standard diet which is a clear sign of an improvement in the state of the exocrine part of the pancreas Zn-64 Asp has a positive effect on the morphological and functional properties of pancreas in animals fed with a high-fat diet The area of hepatocytes decreased on 41% compared to the group with obesity, which indicates a decrease in the deposition of lipid inclusions in hepatocytes An increase in nuclear cytoplasmic ratio by 31% relative to the group with obesity Positive effect of Zn-64 Asp on the state of the liver under the development of obesity demonstrates its perspective efficiency for the treatment of NASH Zn-64 Asp administered to animals on a high-fat diet has a normalization effect on the activity of key enzymes involved in serotonin metabolism, which results in restoration of central and peripheral serotonin levels compared to the values in the untreated animal models of obesity:

An increase in serotonin levels in the brain due to an increase in tryptophan levels and, accordingly, activation of serotonin synthesis Inhibition of an alternative way of its transformation and reduction in the rate of serotonin degradation by monoamine oxidase Zn-64 Asp can be used as monotherapy or in combination with other drugs for the improvement of overall metabolic status under the development of obesity and prevention of the obesity-related disorders The administration of Zn-64 Asp restores prooxidant-antioxidant homeostasis in animals on a high fat diet due to:

Reduction of free radical processes intensity (decrease in the levels of lipid peroxidation products and protein oxidative modification)

Activation of antioxidant defense via increased activity of antioxidant enzymes (superoxide dismutase and catalase).

Results in redistribution of divalent metal ions (zinc, copper, manganese) between muscles, kidneys, and liver in animal models of obesity leading to the restoration of their normal physiological levels.

The preclinical study of the effects of Zn-64 Asp on key pathogenetic links in the development and progression of obesity in diet-induced obesity models provides strong ground for efficient use of Zn-64 Asp as therapeutic agent in the treatment of overweight and obese patients.

Zn-64 Asp normalizes cytokine profile of the serum and adipose tissue in animals on a high-fat diet:

Reduction of pro-inflammatory cytokines (IL-1, IL-6, IL-12, IFN-γ) levels

Increase of anti-inflammatory cytokines (IL-4, IL-10, TGF) levels resulting in a decreased intensity of systemic inflammation.

Administration of Zn-64 Asp results in a drop of glucose concentration compared to the control group.

Zn-64 Asp modulates insulin level in the bloodstream

Zn-64 Asp causes either an increase in the activity of insulin relative to its receptor in tissues or an increase in the amount of this hormone in the bloodstream Zinc-64 either has a more prolonged effect on insulin levels in blood serum or is more slowly released from the sites of deposition compared to Zn-natural Administration of Zn-64 Asp leads to a more than 100% increase of insulin producing pancreatic islets area Administration of Zn-64 Asp results in the improvement of all parameters characterizing the development of type 1 diabetes—the concentration of glucose, glycosylated hemoglobin and insulin content:

A decrease of glucose concentration by 26%

Decrease of glycosylated hemoglobin by 30%

An increase of serum insulin content by 13%

The effect oz Zn-64 Asp on cytokine profile allows to consider it as a modulator for normalization of the inflammatory process that occurs in the body under the development of type 1 diabetes Administration of Zn-64 Asp leads to a reduction of the toxic effect caused by increased glucose concentration in the bloodstream during the development of type 1 diabetes and can be used to treat patients with this metabolic pathology Preclinical data confirms the possibility of using Zn-64 Asp for treating patients who have a pathology of carbohydrate metabolism to 1. Reduce the level of hyperglycemia
2. Restore the structural integrity of the pancreas in pathological conditions of Obesity Type 1 and 2 diabetes Metabolic syndrome Hyperglycemic states of the body of various etiologies Summary of Homeostatic Effect of Zn-64—Aspartate in Rats with LPS—Induced Parkinson's Disease Inhibition of the local and systemic inflammation Prevention of dopaminergic neuron loss in and diminished manifestation of the disease in rodents: weight loss, progressive rotational activity in apomorphine test and cognitive decline virtually full restoration of the number of dopaminergic neurons in the substantia nigra in rats Prevention of microglia metabolic exhaustion in and anti-inflammatory metabolic shift in these cells Inhibition/prevention of systemic inflammation in and anti-inflammatory metabolic shift of circulating phagocytes Facilitation of the resolution of low-grade MALT (Mucosa-Associated Lymphoid Tissue) inflammation Activation of neuronal stem and progenitor cells Positive effect on gut microbiota and gut barrier integrity Restoration of homeostasis—absence of harmful side effects Summary of Homeostatic Effect of Zn-64 Aspartate on Cognitive Activity and Local and Systemic Immune Reactivity in Rat Model of Alzheimer's Disease Induced by Infusion of Aβ 1-40

A decrease in the body weight and a decrease in water and feed intake in rat models of Aβ1-40-induced AD was observed 3 weeks after mimicking the disease. These parameters were restored in AD rats treated with $^{64}$Zn-asp for 10 days.

A decreased number of hippocampal dopaminergic neurons and decreased expression of tyrosine hydroxylase in hippocampal dopaminergic neurons were recorded in rat models of Aβ1-40-induced AD. Administration of $^{64}$Zn-asp to Aβ1-40 AD rats increased the staining intensity of TH-immuno-positive cells rather than their number.

Progression of Aβ1-40-induced AD was associated with impairment of cognitive flexibility in AD rats, which indicates impaired function of the frontal cortex. Rat models of Aβ1-40-induced Alzheimer's disease did not exhibit any changes in their ability to spatial learning or short-term/long-term memories (hippocampal function). Administration of $^{64}$Zn-asp significantly improved the cognitive function in AD models and virtually returned it to the values in intact and sham-operated animals.

Progression of Aβ1-40-induced AD was characterized by a prolonged acute local (in microglia) inflammatory process and a moderately expressed systemic inflammation with signs of its spontaneous resolution. Insignificant manifestation of systemic inflammation in this AD model is its weak point since clinical manifestation of AD is characterized by a pronounced systemic inflammation.

Therapy with the zinc-based test substance resulted in an almost complete resolution of neuroinflammation and homeostatic regulation of systemic immune reactivity, which indicates a pathogenetic nature of its therapeutic effect.

The Rationale and Data for the Use of KLS-1 in the Treatment of Covid-19

The mechanism of KLS-1 ($^{64}$Zn$_e$ aspartate) action is based on the prevention of virus penetration through the receptor—zinc metalloenzyme ACE 2 to a new cells and inhibition of coronavirus reproduction in already affected cells. Homeostasis restoration effect is achieved by the correction of cells proteins production in ribosomes.

The synthesis of KLS—and phase 1-2 study on Covid-19 patients is ready to start. Quantities of KLS-1 enough for the treatment of big number of patents can be produced in a short time.

KLS-1 represents a new platform critical for defeating not only Covid-19 coronavirus but also its possible any future mutant derivatives.

The results obtained in the course of in vitro studies into the effect of composites zinc and its light isotope with different amino acids and solutions on the reproduction of influenza, herpes and surrogate model of HCV (BVDV) viruses indicate that solutions of zinc and its light isotopes effectively inhibit the reproduction of influenza, herpes and surrogate model of HCV (BVDV) viruses.

Zn-64 and Zn-natural solutions in citric acid, Zn-64 and Zn in glutamic acid, and Zn-64 and Zn in glycine-methionine solution were most promising. It is confirmed by:

Inhibition of reproduction of influenza and herpes viruses, Epstein-Barr virus, and surrogate hepatitis C virus (BVDV—bovine viral diarrhea virus).

Absence of influence on the mitotic regime of cells.

Inhibition of RNA and DNA synthesis by citrate and glutamate of the stable light isotope of zinc-64 and Zn-64 glycine-methionine.

Zinc glutamate and zinc-64 light isotope glutamate composites in deuterium-depleted water effectively inhibited the reproduction of influenza, herpes and surrogate hepatitis C viruses, but the efficacy index of light isotope in all viral reproductive systems was several times lower than that of natural zinc since the $CC_{50}$ of light isotopes of Zn in deuterium-depleted water is much higher.

The results of assessment of cytotoxicity and antiviral activity of the preparations under study shows that Zn64 citrate, Zn64 EDDA, Zn64 aspartate, Zn64 glutamate and Zn64 in glycine-methionine are the most promising substances for anti-EBV infection.

Bactericidal Action of Light Isotope $^{64}Zn_e$

To evaluate the bactericidal action of the antibacterial composition based on light isotope $^{64}Zn_e$ the minimum bactericidal concentration (MBC) was determined by plating out 0.1 ml of the contents of each tube containing the antibacterial composition on Mueller-Hinton medium. The incubation was at 37° C. for 24 h.

The MBC of the test samples was determined as the lowest concentration at which there was no growth on Mueller-Hinton agar medium. The established MBC values are given in Table 4.

TABLE 4

The MBC for all samples of the antibacterial composition based on light isotope $^{64}Zn_e$ for test cultures
MBC, mcg $^{64}Zn_e$/ml

| Test culture | $^{64}$Zne citrate | $^{64}$Zne EDDS | $^{64}$Zne sulfate | $^{64}$Zne aspartate | $^{64}$Zne glutamate |
|---|---|---|---|---|---|
| *S. aureus* | 0.028* | 0.73* | 0.37* | 0.023* | 0.046* |
| *E. coli* | 0.44* | 2.93* | 1.46* | 0.73* | 0.37* |
| *P. aeruginosa* | 112.5 | 375 | 375 | >750 | >750 |

*Value is rounded off.

The additional data demonstrated that the antibacterial composition had a pronounced bacteriostatic and bactericidal activity. All samples of the composition had good indicators of bacteriostatic activity against *S. aureus* and *E. coli*. As for *P. aeruginosa*, the best results were recorded for the antibacterial composition which included $^{64}Zn_e$ in the form of salt with EDDA, aspartic acid, and glutamic acid. Bactericidal activity of the antibacterial composition against *S. aureus* and *E. coli* was sufficiently high in all the samples.

TABLE 5

Comparative figures of MIC of samples containing $^{64}Zn_e$ and samples with natural zinc
MIC, zinc mcg/ml

| Test culture | $^{64}Zn_e$ EDDS | Natural zinc - EDDS | $^{64}Zn_e$ sulfate | Natural zinc - sulfate |
|---|---|---|---|---|
| *S. aureus* | 0.73 | 93.75 | 0.366 | 93.75 |
| *E. coli* | 0.18 | 375 | 0.0916 | 187.5 |
| *P. aeruginosa* | 5.86 | 375 | 46.875 | 750 |

TABLE 6

Comparative figures of MBC of samples containing $^{64}Zn_e$ and samples with natural zinc
MBC, mcg zinc/ml

| Test culture | $^{64}Zn_e$ EDDS | Natural zinc as part of EDDS | $^{64}Zn_e$ sulfate | Natural zinc sulfate |
|---|---|---|---|---|
| *S. aureus* | 0.7324 | 375 | 0.3662 | >750 |
| *E. coli* | 2.9296 | >750 | 1.4648 | >750 |
| *P. aeruginosa* | 375 | >750 | 375 | >750 |

The data above show that the antibacterial composition containing $^{64}$Zn-enriched zinc demonstrated a bacteriostatic activity which is significantly higher than that of the natural zinc-based preparations with the natural isotope distribution (by a factor of about 15 to about 2000 maximum). The bactericidal activity of the composition in all cases was significantly higher than that of the preparation containing natural zinc in the form of similar salt. Thus, it was confirmed that the bacteriostatic and bactericidal activities of the antibacterial composition is directly attributable to the presence of light isotope $^{64}$Zn-enriched zinc in the form of a salt of an organic or inorganic acid.

To confirm the effectiveness of the antibacterial composition, a parallel experiment was carried out for its comparison with known antibacterial agents. The following commercial antibacterial medications were used for the study: azithromycin and ceftriaxone and norfloxacin. The initial concentration of 3000 mcg/ml was used for the samples of all the above compounds. The conditions of the experiment were like those for Zn-64 compound. Serial dilutions of the above antibacterial compounds were also prepared in the same way as for the antibacterial composition of the invention. The same pathogenic strains of *S. aureus* ATCC 25923, *E. coli* ATCC 25922, *P. aeruginosa* ATCC 27853 were used for the study. The MIC and MBC established for the antibacterial agents are shown in Tables 7 and 8, respectively.

TABLE 7

MBC of azithromycin, norfloxacin and ceftriaxone against test strains

| Test cultures | MBC, mcg/ml azithromycin | MBC, mcg/ml norfloxacin | MBC, mcg/ml ceftriaxone |
|---|---|---|---|
| S. aureus ATCC 25923 | <1500 | <1500 | 375 |
| E. coli ATCC 25922 | <1500 | <1500 | 11.72* |
| P. aeruginosa ATCC 27853 | <1500 | <1500 | <1500 |

*Value is rounded off to the nearest 0.01.

TABLE 8

MIC of azithromycin, norfloxacin and ceftriaxone against test strains

| Test cultures | MIC, mcg/ml azithromycin | MIC, mcg/ml norfloxacin | MIC, mcg/ml ceftriaxone |
|---|---|---|---|
| S. aureus ATCC 25923 | 187.5 | 11.72* | 11.72* |
| E. coli ATCC 25922 | 1500 | 23.44* | 2.93* |
| P. aeruginosa ATCC 27853 | 1500 | 187.5 | 750 |

*Value is rounded off to the nearest 0.01.

As seen from the above data, the MIC and MBC of the commercial antibacterial agents are much inferior to those of the Zn-64 antibacterial composition, which confirms its efficiency and expediency of application for the control of pathogenic microorganisms. Therefore, the use of KLS-1 in both prevention and therapeutic modes can be decisive factor in winning against Covid-19 as the most dangerous phase of this disease is characterized as viral-bacterial pneumonia with respiratory anatomical space colonized by various bacteria.

Anti-Inflammatory Effect and Homeostatic Effect

Another precious feature of Zn-64 based KLS-1 are strong general anti-inflammatory effect and homeostatic effect. The data was obtained during preclinical studies of the KLS-1 efficacy in treatment of obesity (which also an important complicating factor for Covid-19), Diabetes 1&2, Parkinson's disease, and Alzheimer's disease.

Both anti-inflammatory and homeostatic action of KLS-1 are extremely important for the treatment of Covid-19 patients to prevent or reduce intensity of cytokine storm and reduce inflammation in homeostatic manner without damaging efficiency of the immune system.

There is no doubt that adipose tissue is not only an energy depot of the body, but also an organ that is actively involved in the regulation of metabolism through a complex of endocrine, paracrine and autocrine signals modulating responses of many tissues and organs, including the hypothalamus, hypophysis, pancreas, liver, skeletal muscles, kidneys, endothelium, the immune system, etc. Thus, adipose tissue secretes more than 50 protein factors, hormones, and growth factors, including cytokines. There are pro-inflammatory cytokines, such as IL-1, IL-6, IL-8, IL-12, TNF-α, IFN-γ and anti-inflammatory cytokines, such as IL-4, IL-10, IL-13, TGF.

One of the consequences of excessive production of reactive oxygen species in adipocytes is the initiation of signaling cascades, leading to an increase in the production of pro-inflammatory cytokines by macrophages which infiltrate in adipose tissue increasing in its mass. The result of such disorders is the formation of systemic chronic inflammation in the body of a person that develops obesity. According to the actively discussed modern concept, it is subclinical chronic inflammation in adipose tissue that is thought to be one of the key links in the pathogenesis of obesity and obesity-related diseases. Chronic inflammation of adipose tissue is characterized by cellular infiltration, fibrosis, microcirculation changes, impaired adipokine secretion and adipose tissue metabolism disorders, as well as increased blood levels of such non-specific inflammatory markers as C-reactive protein, fibrinogen, and leukocytes.

An increase in the levels of pro-inflammatory cytokines not only in adipose tissue, but also in blood serum occurs a result of the inflammatory process in adipose tissue.

Cytokines, as endogenous biologically active mediators that regulate intercellular and intersystem interactions, influence the survival of cells by regulating their growth, differentiation, functional activity, and apoptosis. They ensure coordination of actions of the immune, endocrine and nervous systems under physiological conditions and in response to pathological effects. It was previously believed that cytokines were produced by lymphocytes, monocytes and tissue macrophages. However, the results from recent research show that, in obesity, as in any inflammatory process, infiltration of neutrophils, T-lymphocytes, and then resident macrophages into adipose tissue occurs at an early stage, which determines the initial mechanisms of inflammation. It has been shown that macrophages contribute to hypertrophy of adipocytes, which is accompanied by an increase in their functional activity and increased synthesis of cytokines and leads to further intensification of the inflammatory response. Hypertrophied adipocytes intensely secrete chemokines and their receptors, which stimulate the influx of new neutrophils, macrophages and lymphocytes, thus contributing to a further increase in adipocyte hypertrophy, preservation and intensification of the inflammatory response. Adipocytes increase the secretion of cytokines by macrophages, which in turn act on adipocytes, causing hypertrophy and activation of adipose tissue cells. It has been found that hypertrophied adipocytes, like lymphocytes and macrophages, produce cytokines and activate the complement, triggering a chain of inflammatory processes. As a result, the inflammation becomes steady and systemic. In addition, lipid peroxidation products, such as trans-4-oxy-2-nonenal and malonic dialdehyde, are chemo-attractants for monocytes and macrophages. Strengthening of the processes of lipid peroxidation in accumulated adipose tissue contributes to the attraction and infiltration of macrophages into adipose tissue in obesity, thus actively contributing to the launch of inflammation reactions.

Consequently, an increasing adipose tissue mass is a constant source of pro-inflammatory cytokines synthesized both by adipocytes and macrophages incorporated into adipose tissue, which leads to the formation of a chronic inflammatory process and maintenance of inflammation in the body. Its low intensity does not give direct clinical symptoms, but at the same time, this process is systemic in nature, which means that it affects a wide range of organs and tissues causing changes in their metabolism and impairing their function and immune system reactions.

Given the above, the next phase was to find out whether the administration of Zn-64 stable isotope in aspartate form influences the cytokine profile in obese animals. For this purpose, concentrations of the main pro-inflammatory (IL-1, IL-6, IL-12, IFN-γ) and anti-inflammatory (IL-4, IL-10, TGF) cytokines in adipose tissue and serum of experimental animals were determined, which allowed us to make a conclusion about the intensity of the inflammatory process in adipose tissue and assess whether such inflammatory process is systemic.

According to the obtained results, the development of obesity was accompanied by an increase in the levels of all analyzed pro-inflammatory cytokines (Table 9) in the adipose tissue of animals fed a high-fat diet, which indicates activation of the inflammatory process.

In turn, a prolonged inflammatory process may lead to the development of various complications. Intensification inflammatory processes and increased accumulation of inflammatory intermediates may cause tissue damage and organs dysfunction.

increased production of C-reactive protein (CRP), another factor associated with obesity.

One of the controlling mechanisms for the levels and, accordingly, the biological effects of pro-inflammatory cytokines is implemented by a group of anti-inflammatory cytokines. These cytokines can inhibit the synthesis of pro-inflammatory cytokines by affecting transcription of specific genes, induce the synthesis of receptor antagonists of interleukins RAIL, enhance the production of soluble receptors and reduce the density of pro-inflammatory receptors on cells. Therefore, to clarify possible mechanisms of the effects of Zn-64 stable isotope in aspartate form on the profile of pro-inflammatory cytokines, the levels of IL-4, IL-10, and TGF were determined.

TABLE 9

Cytokine profile in the adipose tissue of animals from experimental groups
($M \pm m, n = 10$)

| | Levels, RU/mg protein | | | | | | |
|---|---|---|---|---|---|---|---|
| | Pro- inflammatory cytokines | | | | Anti- inflammatory cytokines | | |
| Groups | IL-1 | IL-6 | IL-12 | IFN-γ | IL-4 | IL-10 | TGF |
| C | 5.6 ± 1.3 | 5.9 ± 0.7 | 1.2 ± 0.03 | 4.7 ± 1.2 | 4.8 ± 0.5 | 4.7 ± 0.7 | 4.5 ± 0.9 |
| C + zinc64 | 4.9 ± 1.7 | 5.4 ± 0.3 | 1.0 ± 0.03 | 5.0 ± 0.8 | 5.0 ± 0.4 | 4.9 ± 0.2 | 5.1 ± 0.6 |
| DIO | 9.8 ± 2.8 * | 8.9 ± 0.7 * | 2.87 ± 0.08 * | 7.6 ± 1.2 * | 3.9 ± 0.2 * | 3.1 ± 0.6 * | 3.1 ± 0.1 * |
| DIO + Zinc64 | 5.8 ± 1.8 # | 6.1 ± 0.7 # | 1.99 ± 0.01 # | 4.9 ± 0.8 # | 5.1 ± 1.2 # | 5.8 ± 0.8 # | 5.2 ± 0.9 # |

\* - the difference is significant versus the control group of animals;
- the difference is significant versus the group of animal models of obesity
Note:
C - control;
C + zinc - control on the background of administration of Zn-64 stable isotope in aspartate form;
DIO - diet induced obesity;
DIO + zinc64 - diet induced obesity on the background of administration of Zn-64 stable isotope in aspartate form.

It has been proven that high levels of pro-inflammatory cytokines, including those mentioned above, can provoke apoptosis of β-cells. High concentrations of IL-12, the expression of which is activated by IFN-γ, lead to infiltration of CD8+ lymphocytes in the pancreas and the development of acute pancreatitis. IL-1B, via binding to specific receptors on the surface of these cells, causes activation of NF-κB-mediated apoptosis, which leads to DNA fragmentation and loss of functional activity of cells. In addition, IL-1B may also be regarded as one of the factors contributing to the development of resistance of peripheral tissues to insulin. IL-1β has been shown to activate IκB kinase-β which influences insulin signaling by phosphorylating a serine residue in the insulin receptor substrate (IRS)-1. In addition, IL-1β can increase resistance to the action of insulin indirectly, by activating lipogenesis in the liver and contributing to an increase in the levels of triglycerides and free fatty acids in adipocytes.

It has been shown that IL-6 is accumulated in direct proportion to an increase in the adipose tissue mass in peripheral blood. Adipocytes are the second largest source of IL-6 after the immune system: 35% of circulating IL-6 is synthesized by adipose cells. Its concentration in the blood is directly proportional to the body mass index and is increased in obesity. At the same time, a decrease in body weight is accompanied by a decrease in the blood levels of IL-6. When in excess, IL-6 exacerbates insulin resistance by suppressing synthesis of one of the insulin receptor subunits. By activating lipolysis in visceral adipose tissue, IL-6 contributes to the progressive development of fatty hepatosis and systemic atherosclerosis. In addition, IL-6 induces Detected changes in the levels of pro-inflammatory cytokines occurred against the background of a slight decrease in the levels of anti-inflammatory cytokines in obese animals. At the same time, in animals treated with Zn-64 stable isotope in aspartate form, the levels of anti-inflammatory cytokines were not only higher than in the untreated animal models of obesity, but also higher than in the animals from the control group.

It should be emphasized that the absence of changes in the animals from the control group treated with the test substance suggests that a long-time use of Zn-64 stable isotope in aspartate form is safe and it is able to show a therapeutic effect only with the development of pathological conditions.

As mentioned above, the pathogenesis of obesity is accompanied by a systemic chronic inflammatory process, the intensity of which can be assessed by the serum levels of pro- and anti-inflammatory cytokines.

Analysis of the cytokine profile in the serum of animals having obesity (Table 10) showed an increase in the levels of pro-inflammatory cytokines, more pronounced compared with the data obtained from adipose tissue. No statistically significant changes in the levels of anti-inflammatory cytokine IL-4 were found. A slight increase in the serum levels of IL-10 in obese animals can be regarded as a certain compensatory response of the body to a metabolic disorder.

In animals treated with Zn-64 based KLS-1 there was a decrease in the levels of pro-inflammatory cytokines against the background of an increase in the levels of anti-inflammatory cytokines, which were even higher than in the animals from the control group.

TABLE 10

Cytokine profile in the serum of animals from experimental groups (M ± m, n = 10)

| | Levels, RU/mg protein | | | | | | |
|---|---|---|---|---|---|---|---|
| | Pro- inflammatory cytokines | | | | Pro- inflammatory cytokines | | |
| Groups | IL-1 | IL-6 | IL-12 | IFN-γ | IL-4 | IL-10 | TGF |
| C | 3.4 ± 0.3 | 4.5 ± 0.3 | 0.5 ± 0.05 | 3.6 ± 0.8 | 5.1 ± 0.2 | 3.9 ± 0.4 | 3.8 ± 0.8 |
| C + Zinc64 | 3.5 ± 0.7 | 4.3 ± 0.2 | 0.3 ± 0.04 | 4.6 ± 0.6 | 4.6 ± 0.8 | 4.1 ± 0.5 | 4.1 ± 0.4 |
| DIO | 11.1 ± 2.0 * | 7.9 ± 0.5 * | .7 ± 0.07 * | 6.5 ± 0.8 * | 4.4 ± 0.9 | 4.1 ± 1.5 | 3.5 ± 1.3 |
| DIO + Zinc64 | 4.2 ± 0.4 # | 5.1 ± 0.4 # | 2.4 ± 0.06 *, # | 4.1 ± 1.2 | 5.6 ± 1.6 | 6.8 ± 1.1 *, # | 5.7 ± 0.3 *, # |

\* - the difference is significant versus the control group of animals;
\# - the difference is significant versus the group of animal models of obesity
Note:
C - control;
C + zinc - control on the background of administration of Zn-64 stable isotope in aspartate form;
DIO - diet induced obesity;
DIO + zinc - diet induced obesity on the background of administration of Zn-64 stable isotope in aspartate form.

One of the basic mechanisms of the effect of zinc on the cytokine profile may be its inhibition of transcription factors sensitive to oxidative stress. Zinc-64 may also partially block genes encoding pro-inflammatory cytokines, such as IL-6 and IL-8.

Anti-inflammatory effect of Zn-64 aspartate (KLS-1) does not depend on the pathogenesis of inflammation. It is a result of the restoration of the healthy homeostasis.

Below is a summary from the in vivo studies:
Effects of $^{64}$Zn-KLS-1 on Local and Systemic Immune Reactivity, Behavioural and Motor Functions in Rats with LPS-Induced Experimental Parkinsonism
1. Progression of LPS-induced Parkinson's disease is accompanied by functional depletion of phagocytosis of microglia caused by a prolonged local inflammatory process. The use of the KLS-1, accompanied by a positive therapeutic effect, was associated with an increase in the metabolic activity of microglia with a significant activation of their phagocytic function involved in reparative processes, which is indicative of the restorative homeostatic effect of the KLS-1.
2. Progression of LPS-induced parkinsonism is accompanied by pronounced peripheral inflammation, as evidenced by mono-cytosis in combination with an increase in the neutrophil-lymphocyte ratio. Therapeutic administration of the KLS-1 reduces systemic inflammatory responses.
3. Phenotypic and metabolic characteristics of circulating phagocytes indicate their functional depletion caused by prolonged systemic inflammatory process, simultaneously with a proinflammatory shift in their functional activity. Administration of the KLS-1 is accompanied by a functional restoration of circulating phagocytes with an anti-inflammatory shift in their metabolism.
4. Progression of LPS-induced parkinsonism is accompanied by involvement of MALT immunocytes in the generalized inflammatory process with their proinflammatory activation. Administration of the KLS-1 induces homeostatic changes in metabolism in these cells with their proinflammatory metabolic shift.

An additional proof of homeostatic anti-inflammatory effect was obtained in this study:
The Effect of $^{64}$Zn-Asp on Cognitive Symptomatology in Rats with Different Models of Alzheimer's Disease Induced by Infusion of a Mix of Beta-Amyloid Peptides Inflammation and homeostasis related findings summary are as follows.

1. The development of AD induced by Aβ 1-40 infusion was characterized by a prolonged acute local (in microglia) inflammatory process and a moderately expressed systemic manifestation of inflammation with signs of its spontaneous resolution. A slight manifestation of systemic inflammation in this model is its weak point since clinical manifestation of AD is characterized by a pronounced systemic inflammation.
2. The therapeutic administration of a zinc preparation of actuators of an almost complete resolution of neuroinflammation and homeostatic regulation of systemic immune reactivity, which indicates the pathogenetic nature of its therapeutic effect.
3. Literature data convincingly indicate that chronic inflammation is one of the most important pathophysiological components of synucleinopathies and taupathies, including AD. The leukogram of patients with AD reveals an increased number of monocytes and neutrophils. At the same time, the number of lymphocytes is reduced in comparison with the norm. An increased number of monocytes and neutrophils are signs of chronic inflammation and can both precede AD and be its consequence. A low number of lymphocytes indicates that the body's resistance to the fight against infection is significantly reduced. An increase in BBB permeability in AD facilitates the migration of neuroinflammatory mediators to the periphery. As well as recruiting circulating leukocytes to the brain, which creates the prerequisites for the persistence of the meta-inflammatory process. The study of hematological parameters was carried out at the time of completion of the experiment.
4. Analysis of the hemogram of animals with Aβ 1-40 model of AD showed a sharp leukocytosis: the number of circulating leukocytes compared to intact animals was increased 2.5 times. It should be noted that expressive leukocytosis was also observed in the placebo group, which is apparently due to the low reparative potential of the immune system in old animals. The therapeutic administration of a microelement preparation was accompanied by a complete normalization of the absolute number of circulating leukocytes in animals with AD. The characteristics of the population composition of circulating leukocytes showed a slight decrease in the number of lymphocytes and a significant decrease in the number of monocytes (moderate monocytopenia). AD induction was also accompanied by expressive neutrophilia with a significant (more than 4-fold) increase in the neutrophilic lymphocytic coefficient (the ratio of the absolute number of neutrophils to the absolute number of peripheral blood lymphocytes, NLC). NLC is one of the early markers of AD development and an important prognostic criterion for cognitive impairment. The therapeutic administration of the zinc preparation was associated with the complete normalization of NLC, both due to an increase in the number of lymphocytes (which is a criterion for the resolution of inflammation involving regulatory cells), and due to a significant decrease in the number of segmented neutrophils.

The effectiveness of isotope selective therapy is because this therapy unlike existing treatments acts on the root cause of pathology: isotope substitution induced distortion of helices in proteins structure, the emergence of D-amino acids in proteins, changes in their conformation, unfolding and aggregation. Zinc fingers in ribosomes play critical role in the onset of pathogenesis. Ribosomes produce all proteins. The essence of this technology is to change isotope ratios of zinc in these biomolecules creating necessary conditions for the wild type proteins production. All proteins. How can one tell if it works? After all, it is quite difficult to test conformation of 20,000 proteins in humans. At the same time, pathology affected live cells are enriched in heavy isotopes and healthy cells with normal proteins must be enriched in light isotopes. In this case, the replacement of heavy zinc isotopes in ribosomes by Zn-64 should guarantee the synthesis of wild type proteins enriched with light isotopes. This also applies to metalloproteins. Therefore, the easiest way to check the fundamentals of this technology—by the verification of the isotope ratios of essential chemical elements in any organ of animal after Zn-64 infusion. Once again, even though it is intended to increase concentration of Zn-64 in the blood stream, the isotope ratios shift should be detected in favor of lightest ones not only in zinc but in other metals as well. If so, then it's unheard of. To simultaneously check whether the test small molecule penetrates through blood-brain barrier isotope ratios have been studied in two groups of mice: control group of healthy mice with no treatment and therapeutic on after 10 daily I.V. infusions of Zn-64 aspartate. The results in the table below are in complete agreement with prediction.

TABLE 11

Effect of 10 I.V. daily Zn-64 aspartate injections on isotopes ratios in mice brains six samples per brain

| | Control/No Injections | | | Natural | After Injections | | |
|---|---|---|---|---|---|---|---|
| | Min | Max | Average | Abundance | Average | Max | Min |
| Zn64 | 49.07 | 54.94 | 53.12 | 48.60 | 58.44 | 58.99 | 57.87 |
| Zn66 | 24.06 | 25.06 | 24.14 | 27.90 | 28.44 | 28.55 | 28.21 |
| Zn67 | 3.10 | 4.09 | 3.86 | 4.10 | 1.04 | 1.22 | 0.94 |
| Zn68 | 15.22 | 17.32 | 16.28 | 18.80 | 11.48 | 11.74 | 11.32 |
| Zn70 | 0.55 | 0.66 | 0.60 | 0.60 | 0.60 | 0.75 | 0.46 |
| Mg24 | 78.29 | 81.72 | 80.13 | 78.99 | 82.50 | 83.95 | 81.32 |
| Mg25 | 8.13 | 10.86 | 9.96 | 10.00 | 8.94 | 9.48 | 8.35 |
| Mg26 | 9.22 | 11.24 | 10.21 | 11.01 | 8.56 | 8.79 | 8.32 |
| Fe54 | 5.78 | 6.85 | 6.14 | 5.80 | 7.95 | 8.85 | 7.34 |
| Fe56 | 91.26 | 91.81 | 91.55 | 91.72 | 91.99 | 92.68 | 91.61 |
| Fe57 | 1.80 | 2.20 | 2.02 | 2.20 | 0.22 | 0.55 | 0.00 |
| Fe58 | 0.28 | 0.28 | 0.28 | 0.28 | 0.28 | 0.28 | 0.28 |
| K39 | 89.45 | 92.46 | 90.89 | 93.26 | 95.50 | 96.80 | 94.45 |
| K41 | 8.36 | 10.04 | 9.11 | 6.74 | 4.50 | 4.99 | 4.16 |
| Rb85 | 69.42 | 71.80 | 70.81 | 72.16 | 76.66 | 76.78 | 76.42 |

TABLE 11-continued

Effect of 10 I.V. daily Zn-64 aspartate injections on isotopes ratios in mice brains six samples per brain

| | Control/No Injections | | | Natural | After Injections | | |
|---|---|---|---|---|---|---|---|
| | Min | Max | Average | Abundance | Average | Max | Min |
| Rb87 | 28.22 | 29.58 | 29.19 | 27.84 | 23.34 | 23.82 | 23.01 |
| Si28 | 91.62 | 94.21 | 92.64 | 92.23 | 93.40 | 93.88 | 92.27 |
| Si29 | 3.81 | 4.84 | 4.46 | 4.57 | 4.36 | 4.57 | 4.02 |
| Si30 | 3.01 | 3.09 | 2.88 | 3.10 | 2.24 | 2.83 | 1.82 |

The studies in the Section detailed above were done by administering enriched zinc64 compositions as pharmaceutical compositions and not as food.

Based on the analysis of isotope ratios and proposed mechanism of isotope separation, proteins in the healthy living cell should contain only the lightest isotopes of hydrogen, oxygen, nitrogen, carbon essential chemical elements. Potassium and rubidium, whether they bind to proteins or are playing other roles in cell's life, are required to be in the form K-39 and Rb-85 isotopes. All chemical elements coming into the body with food have isotope ratios in accordance with their well-known natural abundance. Exactly this ratio should be expected to be in the cell's cytoplasm. Protein accounts for approximately 20 percent of a cell's total weight. Lodish H, Berk A, Zipursky S L, et al. Molecular Cell Biology. 4th edition. Section 1.2 New York: W. H. Freeman; 2000. In case light isotopes are used in the protein's production, the isotope ratios in cytoplasm should be shifted in favor of heavy ones leaving total average values per cell equal to the one of incoming into the cell. Some cell must produce proteins/polypeptides "for export," like hormones, cytokines or signaling molecules or breast milk components, for example. Then, the very ability of the cell machinery to produce biomolecules "for export" depends on the materials delivered into the cell. Deficiency in timely supplies of light isotopes would lead to the enrichment of the cytoplasm with heavy isotopes, use of these isotopes in the proteins production and inevitable degradation of the products quality: distortion of helices, tendency to the racemization of amino acids in proteins, their damaged conformation, unfolding and possibly aggregation and loss of function. Therefore, exactly these kinds of cells represent the best place for the onset of pathological changes in tissues and organs, including primary or metastatic cancers. It is logical to assume that in accordance with the "original design" human body should be made of light isotopes only. The problem is that food consists of chemical elements that are mostly mixtures of stable isotopes in proportions to their natural abundance. It means that the primary source of health problems is nutrition, which is in fact a mixture of poison and antidote. That is why people are destined for chronic and/or acute general and local degeneration. Treatment and prevention of degenerative and infectious diseases require sufficient supply of light isotopes like Zn-64, K-39, Mg-24, or Fe-54, for example. The use of intravenous injections or oral pills with light isotopes compositions exceeding daily consumption dose by a factor of 2-4 for prophylactices of degenerative and infectious diseases can be extremely helpful. The efficacy of such approach depends on dose and drugs delivery time. The problem is that this approach cannot prevent heavy isotopes coming with food. The best solution of this problem is to consume isotope selective foods/agricultural products grown in soil fertilized with light isotopes of essential chemical elements. The lightest stable isotopes of essential chemical elements in therapeutic and preventive compounds with various salts and amino acids or biomolecules as vehicles should be used. At the same time, it is well-known that the best vehicles are chemical compounds in plant foods.

It does not make sense to grow plants in soil for agricultural products with any currently known medical drugs: vaccines, antibiotics, inhibitors, activators, and even most sophisticated products like CAR-T cells as they simply decompose in the ground.

In contrast, salts and amino acids based therapeutic compounds enriched with lightest isotopes of essential chemical elements can be used as a new type of nutrients or "fertilizers" in the process of agricultural production of various crops, fruits, and vegetables. They may serve as a part of hydroponic nutrient culture medium to produce sprouts or vegetables or to use fast growing plants with subsequent transformation into a compost enriched with lightest stable isotopes of essential chemical elements. This compost in turn can be used as a main component of the soil to grow plants on. Anti-viral and anti-bacterial action of light isotopes provide additional protection for the plants growing on this soil from bacteria and viruses. Products grown in this manner have a unique prophylactic and therapeutic properties. These plants or trees would have the same properties as the Tree of Life. Thus, food becomes our medicine in accordance with the famous Hippocrates expression. The food humans currently consume consists of isotopes in natural abundance and is in fact a mixture of poisons and antidotes. Daily consumption of isotope-selective food is the best way for continuous maintenance of youthful homeostasis i.e. stability of human organism with simultaneous prevention from degenerative and infectious diseases. Daily consumption doses for essential chemical elements taken with foods are equal to the therapeutic doses determined during phase 1-2 clinical study in patients with metastatic solid tumors, autoimmune diseases, diabetes 1&2, obesity, aphasia, and Parkinson's disease.

EXAMPLES

For this invention to be better understood, the following examples are set forth. These examples are for purposes of illustration only and are not to be construed as limiting the scope of the invention in any manner.

Example 1. Plants Grown in Hydroponics

Plants producing plant products (crops) are grown in hydroponics with a solution comprising lightest isotopes of essential chemical elements in specified concentrations, as shown in Table 12.

TABLE 12

| Crop | K-39 | Ca-40 | Mg-24 | Zn-64 | Fe-54 |
|---|---|---|---|---|---|
| | | Concentration in mg/l (ppm) | | | |
| Tomato | 300 | 160 | 50 | 0.6 | 5 |
| Cucumber | 270 | 150 | 40 | 0.5 | 4 |
| Pepper | 200 | 150 | 45 | 0.4 | 3 |
| Melon | 250 | 160 | 40 | 0.4 | 4 |
| Strawberry | 40 | 140 | 40 | 0.4 | 3 |

The solution is changed either on a schedule, such as once per week, or when the concentration of one or more nutrients drops below a certain level as determined with an electrical conductivity meter. Whenever the solution is depleted below a certain level, either water or fresh solution is added, with the solution comprising light isotopes of essential chemical elements as shown in Table 12. The plant products (crops) are harvested when ready. Food is prepared for human consumption from the products of these plants.

The plants, the plant products, and the food made from these plants/plant products can be verified to comprise enriched light isotopes of K-39, Ca-40, Mg-24, Zn-64, and Fe-54 by methods conventional in the art, such as by mass spectrometry.

Example 2. Plants Grown in Soil with Enriched Zn-64 as Fertilizer

As follows from the data in Table 11 above, ten I.V. injections of Zn-64 enriched to 99.9% lead to the shift of isotope ratios of other essential chemical elements in favor of lightest isotopes. Therefore, growing plants on soil fertilized with just one isotope Zn-64 is greatly beneficial.

Fertilizer comprising Zo-64 sulfate is added to soil before planting plants in the soil or while the plants have not fully grown, Other dry fertilizer materials may also be added to the soil. Any salts or chelates of Zn-64 can be used as fertilizer. Zn-64 sulfate is used in this example. One pound of Zinc-64 per acre is added. Plants are then planted in this soil. The fertilizer comprising Zn-64 sulfate may be added to the soil over time, either when the level of Zn-64 sulfate in the soil is low or on a schedule. The plants or plant products are harvested when ready. Food may be prepared from the plants or plant products for human consumption.

The plants, the plant products, and the food made from these plants/plant products can be verified to comprise enriched Zn-64 and may comprise enriched light isotopes of other essential chemical elements by methods conventional in the art, such as by mass spectrometry.

Example 3. Plants Grown by Foliar Feeding

Zn-64 is supplied to the plant crops through foliar feeding. For this purpose, powdered Zinc-64 sulfate is dissolved in an aqueous solution and sprayed on the leaves of the plants as they grow. 25 gallons of solution per acre should contain from 1.5 to 3 pounds of Zn-64 sulfate to deliver from 0.5 to 1 pound of Zn-64 per acre. The plants or plant products are harvested when ready. Food may be prepared from the plants or plant products for human consumption.

The plants, the plant products, and the food made from these plants/plant products can be verified to comprise enriched Zn-64 and may comprise enriched light isotopes of other essential chemical elements by methods conventional in the art, such as by mass spectrometry.

Example 4. Livestock

Pigs and chickens are fed a diet with food comprising Zn-64 as they grow. Any salts or chelates of Zn-64 can be used, such as Zinc64 Aspartate. Eggs from the chickens are collected and may be consumed. The pigs, the chickens, the eggs from the chickens, and food made from the pigs and chickens can be verified to comprise enriched Zn-64 and may comprise enriched light isotopes of other essential chemical elements by methods conventional in the art, such as by mass spectrometry.

Example 5 Aquaculture

Fresh water fish, such as trout, grown in aquaculture are fed a solution comprising Zn-64 as they grow. Any salts or chelates of Zn-64 can be used, such as Zinc64 Aspartate. The trout can be verified to comprise enriched Zn-64 and may comprise enriched light isotopes of other essential chemical elements by methods conventional in the art, such as by mass spectrometry.

Example 6. Mariculture

Salt water fish, such as sea bass, grown in aquaculture are fed a solution comprising Zn-64 as they grow. Any salts or chelates of Zn-64 can be used, such as Zinc64 Aspartate. The sea bass can be verified to comprise enriched Zn-64 and may comprise enriched light isotopes of other essential chemical elements by methods conventional in the art, such as by mass spectrometry.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A livestock or a livestock product made by a method of making a livestock or a livestock product comprising:
   growing said livestock by feeding said livestock food comprising essential chemical elements enriched for lightest stable isotope or isotopes thereof wherein the enriched stable isotopes of essential chemical elements are more than one selected from the group consisting of $^{24}$Mg, $^{74}$Se, $^{64}$Zn, $^{85}$Rb, $^{28}$Si, $^{54}$Fe, and $^{40}$Ca.

2. The livestock or a livestock product of claim 1, wherein the enriched stable isotopes of essential chemical elements comprise 64Zn, wherein said 64Zn is enriched to be at least 80% $^{64}$Zn.

3. The livestock or a livestock product of claim 2, wherein the $^{64}$Zn is in a form of salt selected from the group consisting of aspartate, sulfate, and citrate.

4. The livestock or a livestock product of claim 3, wherein the $^{64}$Zn is in a form of $^{64}$Zn aspartate with chemical formula of $C_4H_5O_4N^{64}Zn_e$ with 2 aspartic acid molecules.

5. The livestock or a livestock product of claim 1, wherein the livestock product is milk or egg.

6. The livestock or a livestock product of claim 1, wherein the livestock is a pig or a chicken.

7. The livestock or a livestock product of claim 1, wherein said food is fed to the livestock daily.

* * * * *